(12) United States Patent
Lietzau et al.

(10) Patent No.: US 7,922,934 B2
(45) Date of Patent: Apr. 12, 2011

(54) S-INDACENE AND INDENO[5,6-D][1,3]DIOXOL-DERIVATIVES AND USE THEREOF AS COMPONENTS OF LIQUID-CRYSTAL MIXTURES

(75) Inventors: Lars Lietzau, Darmstadt (DE); Detlef Pauluth, Ober-Ramstadt (DE); Markus Czanta, Darmstadt (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 572 days.

(21) Appl. No.: 11/996,202

(22) PCT Filed: Jul. 11, 2006

(86) PCT No.: PCT/EP2006/006771
§ 371 (c)(1),
(2), (4) Date: Jan. 18, 2008

(87) PCT Pub. No.: WO2007/009636
PCT Pub. Date: Jan. 25, 2007

(65) Prior Publication Data
US 2010/0155662 A1    Jun. 24, 2010

(30) Foreign Application Priority Data

Jul. 20, 2005 (DE) .................. 10 2005 033 803

(51) Int. Cl.
*C09K 19/00* (2006.01)
*C09K 19/06* (2006.01)
*C09K 19/52* (2006.01)

(52) U.S. Cl. ........... 252/299.6; 252/299.01; 252/299.61; 252/299.62; 549/433; 570/129; 349/182; 349/183; 349/184; 349/185; 349/186; 428/1.1

(58) Field of Classification Search ............. 252/299.01, 252/299.6, 299.61, 299.62; 549/433; 570/129; 349/182–186; 428/1.1
See application file for complete search history.

(56) References Cited

U.S. PATENT DOCUMENTS

| 2004/0171866 A1 | 9/2004 | Reiffenrath et al. |
| 2006/0165915 A1 | 7/2006 | Lietzau et al. |

FOREIGN PATENT DOCUMENTS

| DE | 39 08 269 A1 | 9/1990 |
| DE | 101 35 499 A1 | 1/2003 |
| EP | 1 350 780 A1 | 10/2003 |
| WO | WO 03/010120 A1 | 2/2003 |
| WO | WO 2004/020375 A1 | 3/2004 |

*Primary Examiner* — Geraldina Visconti
(74) *Attorney, Agent, or Firm* — Millen, White, Zelano & Branigan, P.C.

(57) ABSTRACT

The invention relates 1,2,3,6,7,8-hexahydro-s-indacene derivatives and 6,7-dihydro-5H-indeno[5,6-d]-1,3-dioxole derivatives, and to the use thereof as component(s) in liquid-crystalline media. In addition, the present invention relates to liquid-crystal and electro-optical display elements which contain the liquid-crystalline media according to the invention.

14 Claims, No Drawings

S-INDACENE AND INDENO[5,6-D][1,3]DIOXOL-DERIVATIVES AND USE THEREOF AS COMPONENTS OF LIQUID-CRYSTAL MIXTURES

The invention relates to 1,2,3,6,7,8-hexahydro-s-indacene derivatives and 6,7-dihydro-5H-indeno[5,6-d]-1,3-dioxole derivatives, and to the use thereof as component(s) in liquid-crystalline media. In addition, the present invention relates to liquid-crystal and electro-optical display elements which contain the liquid-crystalline media according to the invention.

The compounds according to the invention can be used as component(s) of liquid-crystalline media, in particular for displays based on the principle of the twisted cell, the guest-host effect, the effect of deformation of aligned phases DAP or ECB (electrically controlled birefringence), the IPS (in-plane switching) effect or the effect of dynamic scattering.

The specification DE 10135499 A1 discloses a 1,2,3,6,7,8-hexahydro-s-indacene skeleton with substituents in positions 1, 7 and 8. The substances have without exception negative values of the dielectric anisotropy Δε.

The specification DE 3908269 A1 discloses 1,2,3,6,7,8-hexahydro-s-indacenes which carry precisely one substituent in each of positions 2 and 6. In addition, Patent Application EP 1350780 A1 discloses 1,7-dihydro-s-indacenes having a plurality of optional substituents which are positioned in such a way that again only compounds having negative values of the dielectric anisotropy Δε are involved.

The present invention was based on the object of finding novel and stable compounds which are suitable as components of liquid-crystalline media. In particular, the compounds should simultaneously have comparatively low viscosity and a dielectric anisotropy in the positive region. For many current mixture concepts in the area of liquid crystals, it is advantageous to use compounds having a particularly high dielectric anisotropy Δε.

With respect to the very wide variety of areas of application of such compounds of high Δε, it was desirable to have available further compounds, preferably of high nematogeneity, which have properties precisely customised to the particular applications.

One object of the invention was thus to find novel, stable compounds which are suitable as component(s) of liquid-crystalline media, in particular for TN, STN, IPS and further TFT displays.

A further object of the present invention was to provide compounds which have a high dielectric anisotropy Δε, a high clearing point and low rotational viscosity $\gamma_1$. in addition, the compounds according to the invention should be thermally and photochemically stable. Furthermore, the compounds according to the invention should be usable in liquid-crystalline mixtures in that they can be dissolved in conventional mixtures and do not impair or even improve the liquid-crystalline phase ranges thereof.

Surprisingly, it has been found that the 1,2,3,6,7,8-hexahydro-s-indacene and 6,7-dihydro-5H-indeno[5,6-d]-1,3-dioxole derivatives according to the invention are eminently suitable as components of liquid-crystalline media. They can be used to obtain stable liquid-crystalline media, in particular suitable for TN-TFT, STN and IPS displays. The compounds according to the invention are stable chemically, thermally and to (UV) light. They are colourless in the pure state. They are also distinguished by strongly positive dielectric anisotropies Δε, due to which lower threshold voltages are necessary in the application in optical switching elements. In addition, the compounds have favourable, i.e. low, values for the rotational viscosity.

Liquid-crystalline media having very low values of the optical anisotropy are of importance, in particular, for reflective and transflective applications, i.e. applications in which the respective LCD experiences no or only supporting backlighting. It is then also possible to obtain liquid crystals according to the invention and mixtures comprising the derivatives according to the invention having very low values of the optical anisotropy or having slightly positive to strongly positive values of the dielectric anisotropy.

The provision of the 1,2,3,6,7,8-hexahydro-s-indacene and 6,7-dihydro-5H-indeno[5,6-d]-1,3-dioxole derivatives according to the invention very generally considerably broadens the range of liquid-crystalline compounds which are suitable, from various applicational points of view, for the preparation of liquid-crystalline mixtures.

When mixed with suitable co-components, the compounds according to the invention form liquid-crystalline mesophases in a temperature range which is favourably located for electro-optical use. Liquid-crystalline media having broad nematic phase ranges can be prepared from the compounds according to the invention and further substances.

The 1,2,3,6,7,8-hexahydro-s-indacene and 6,7-dihydro-5H-indeno[5,6-d]-1,3-dioxole derivatives have a broad range of applications. Depending on the choice of substituents, these compounds can serve as base materials of which liquid-crystalline media are predominantly composed. However, it is also possible to add liquid-crystalline base materials from other classes of compound to the compounds according to the invention in order, for example, to modify the dielectric and/or optical anisotropy of a dielectric of this type and/or to optimise its threshold voltage and/or its viscosity.

The present invention thus relates to 1,2,3,6,7,8-hexahydro-s-indacene and 6,7-dihydro-5H-indeno[5,6-d]-1,3-dioxole derivatives of the general formula I

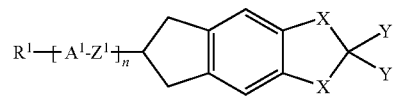

in which $R^1$ denotes H, halogen, a linear or branched, optionally chiral alkyl radical having 1 to 15 C atoms which is unsubstituted, monosubstituted by CN or $CF_3$ or at least monosubstituted by halogen and in which one or more $CH_2$ groups may each, independently of one another, be replaced by —O—, —S—, —CO—, —(CO)O—, —CH=CH—, —CH=CF—, —CF=CF—, —C≡C—, —CH$_2$O— or —CF$_2$O— in such a way that heteroatoms are not linked directly to one another and asymmetrical groups may be present in both orientations, $A^1$ in each case, independently of one another, identically or differently, denotes
 a) trans-1,4-cyclohexylene, in which, in addition, one or more non-adjacent $CH_2$ groups may be replaced by —S—, tetrahydropyran-2,5-diyl or 1,3-dioxane-2,5-diyl,
 b) 1,4-phenylene, in which one or two CH groups may be replaced by N and in which one or more H atoms may be replaced by halogen, preferably by F, c) a radical from the group 1,4-bicyclo[2.2.2]octylene, spiro[3.3]heptane-2,6-diyl, cyclobutane-1,3-diyl, piperidine-1,4-diyl, naphthalene-2,6-diyl, decahydronaphthalene-2,6-diyl and 1,2,3,4-tetrahydronaphthalene-2,6-diyl, in which, in addition, CH may be replaced by N or also one or more H atoms may be replaced by halogen, preferably by F, or d) 1,4-cyclohexenylene, optionally substituted by F, X denotes —CH$_2$—, —CF$_2$— or —O—, Y denotes F, Cl, CF$_3$, CN, NCS, SCN, SF$_5$ or 2- to 6-C perfluoroalkyl, $Z^1$ in each case, independently of one another, in the case of asymmetrical bridging units $Z^1$ in either of the two orientations, denotes a single bond, —CH$_2$O—, —(CO)O—, —CF$_2$O—, —CF=CF—, —CH$_2$CH$_2$CF$_2$O—, —CF$_2$CF$_2$—, —CH$_2$CF$_2$—, —CH$_2$CH$_2$—, —CH=CH—, —CH=CF— or and n denotes 0, 1, 2 or 3.

The present invention furthermore relates to the use of compounds of the formula I as component(s) in liquid-crystalline media.

The present invention likewise relates to liquid-crystalline media having at least two liquid-crystalline components which comprise at least one 1,2,3,6,7,8-hexahydro-s-indacene or 6,7-dihydro-5H-indeno[5,6-d]-1,3-dioxole derivative of the formula I.

The present invention also relates to liquid-crystal display elements, in particular electro-optical display elements, which contain, as dielectric, a liquid-crystalline medium according to the invention.

The meaning of the formula I encompasses all isotopes of the chemical elements bonded in the compounds of the formula I. In enantiomerically pure or enriched form, the compounds of the formula I are in principle also suitable as chiral dopants and in general for achieving chiral mesophases.

Above and below, $R^1$, $A^1$, $Z^1$, X, Y and n have the meanings indicated, unless expressly stated otherwise. If the radicals $A^1$ and $Z^1$ occur more than once, they may, independently of one another, adopt identical or different meanings.

For the sake of simplicity, Cyc below denotes a 1,4-cyclohexyl-1,4-diyl radical, Che denotes an (optionally monofluorinated) cyclohexene-1,4-diyl radical, Dio denotes a 1,3-dioxane-2,5-diyl radical, Thp denotes a tetrahydropyran-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical, Bco denotes a bicyclo[2.2.2]-octylene radical, Cbl denotes a 1,3-cyclobutylene radical, Bpi denotes a spiro[3.3]heptane-2,6-diyl radical and Dec denotes a decahydronaphthalene radical, where Cyc and/or Phe may be unsubstituted or mono- or polysubstituted by F, Cl, CF$_3$, OCF$_3$ and/or CN.

Preference is given to compounds of the formula I in which $R^1$ denotes H, a linear alkyl or alkoxy radical having 1 to 12 C atoms or a linear alkenyl or alkenyloxy radical having 2 to 12 C atoms.

If $R^1$ is halogen, it preferably denotes F or Cl, particularly preferably F.

$A^1$ preferably denotes Phe, Cyc, Che, Pyd, Pyr, Dio or Thp and particularly preferably Phe or Cyc. Preference is furthermore given to compounds of the formula I which contain not more than one of the radicals Dio, Thp, Dit, Pyd, Pyr, Cbl, Spi or Bco.

If the ring $A^1$ is present twice, the two rings may have identical or different meanings. The same also applies to the bridge $Z^1$.

Phe is preferably

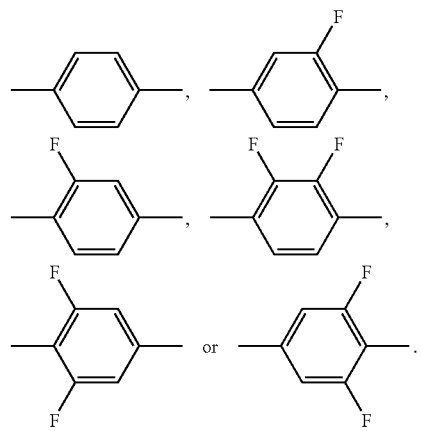

Phe is particularly preferably

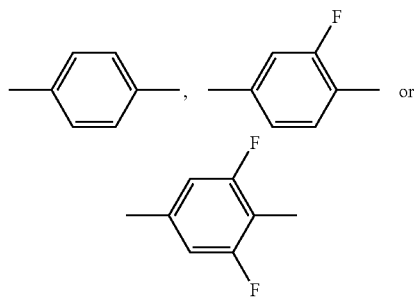

The terms 1,3-dioxane-2,5-diyl and Dio each encompass the two positional isomers

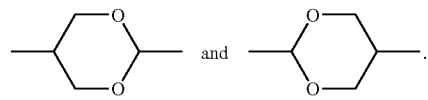

The terms tetrahydropyran-2,5-diyl and Thp each encompass the two positional isomers

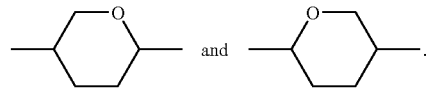

The cyclohexene-1,4-diyl group (Che) preferably has the following structures:

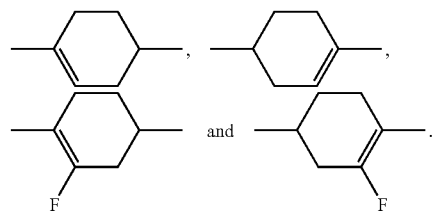

Y is preferably F, CN, CF$_3$ or OCF$_3$, particularly preferably F or CF$_3$.

$Z^1$ preferably denotes —CH$_2$CH$_2$—, —CH=CH—, —C≡C—, —CF$_2$CF$_2$—, —CF=CF—, —(CO)O—, —O(CO)—, —CF$_2$O— or a single bond, particularly preferably —CF$_2$O—, —CH$_2$CH$_2$— or a single bond. In the case where n is >1, at least one of $Z^1$ preferably denotes a single bond.

n is preferably 0, 1 or 2, particularly preferably 0 or 1. If one of $Z^1$ is equal to the group —CF$_2$O—, then n is particularly preferably 2 and the moiety -[$A^1$-$Z^1$]$_n$— preferably stands for -$A^1$-CF$_2$-O-Phe-, where Phe is as defined above.

The compounds of the formula I and sub-formulae thereof according to the invention can also be written in the form $R^1$-[$A^1$-$Z^1$]$_n$—W, where W stands for the fused ring system consisting of the moiety of the formula

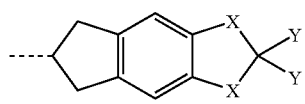   W

Preferred meanings of the structural element W arise from the preferred values for X and Y. Particularly preferred combinations of X and Y result, in particular, in the particularly preferred implementations of the moiety W of the sub-formulae (1) to (5):

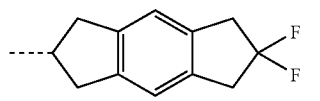   (1)

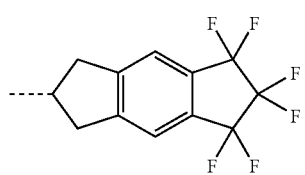   (2)

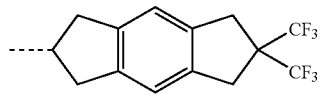   (3)

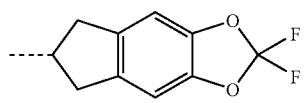   (4)

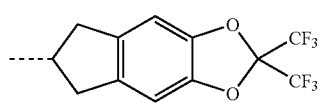   (5)

Besides the case where n is equal to 0, the compounds of the formula I also encompass compounds having one or more rings in the mesogenic group $R^1$-[$A^1$-$Z^1$]$_n$—, as indicated below:

compounds having precisely one ring in the mesogenic group $R^1$-[$A^1$-$Z^1$]$_n$— of the sub-formulae Ia and Ib:

| | |
|---|---|
| $R^1$-$A^1$-W | Ia |
| $R^1$-$A^1$-$Z^1$—W | Ib | compounds having two rings in the mesogenic group $R^1$-[$A^1$-$Z^1$]$_n$— of the sub-formulae Ic to If:

| | |
|---|---|
| $R^1$-$A^1$-$A^1$-W | Ic |
| $R^1$-$A^1$-$A^1$-$Z^1$—W | Id |
| $R^1$-$A^1$-$Z^1$-$A^1$-W | Ie |
| $R^1$-$A^1$-$Z^1$-$A^1$-$Z^1$—W | If | and compounds having three rings in the mesogenic group $R^1$-[$A^1$-$Z^1$]$_n$— of the sub-formulae Ig to Io:

| | |
|---|---|
| $R^1$-$A^1$-$A^1$-$A^1$-W | Ig |
| $R^1$-$A^1$-$Z^1$-$A^1$-$A^1$-W | Ih |
| $R^1$-$A^1$-$A^1$-$Z^1$-$A^1$-W | Ii |
| $R^1$-$A^1$-$A^1$-$A^1$-$Z^1$—W | Ij |
| $R^1$-$A^1$-$Z^1$-$A^1$-$Z^1$-$A^1$-W | Ik |
| $R^1$-$A^1$-$Z^1$-$A^1$-$A^1$-$Z^1$—W | Im |
| $R^1$-$A^1$-$A^1$-$Z^1$-$A^1$-$Z^1$—W | In |
| $R^1$-$A^1$-$Z^1$-$A^1$-$Z^1$-$A^1$-$Z^1$—W | Io |

Of these, particular preference is given to those of the sub-formulae Ia, Ib, Ic, Id, Ie, Ig, Ih, Ii and Ij, very particularly those of the formulae Ia, Ib, Ic, Id and Ii. Preference is thus given to the formulae in which $Z^1$ is always a single bond or only once is not a single bond. At the same time, particular preference is given to the case where n is equal to 0, i.e. a compound of the formula $R^1$—W.

The preferred compounds of the sub-formula Ia encompass those of the sub-formulae Iaa to Iaf:

| | |
|---|---|
| $R^1$-Phe-W | Iaa |
| $R^1$-Cyc-W | Iab |
| $R^1$-Thp-W | Iac |
| $R^1$-Dio-W | Iad |
| $R^1$-Cbl-W | Iae |
| $R^1$-Spi-W | Iaf |

Of these, particular preference is given to those of the following sub-formulae:

   Iaa1

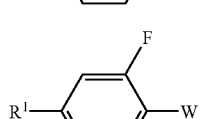   Iaa2

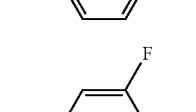   Iaa3

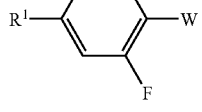

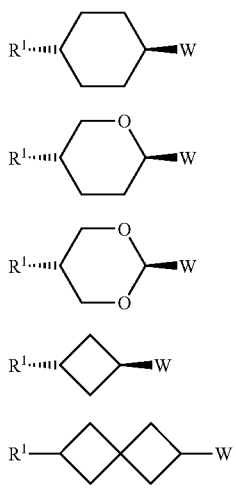

The preferred compounds of the sub-formula Ib encompass those of the sub-formulae Iba and Ibb:

$R^1$-Phe-$Z^1$—W   Iba $R^1$-Cyc-$Z^1$—W   Ibb

For the compounds of the formulae Iba and Ibb, $Z^1$ is preferably —CH$_2$CH$_2$— and Phe preferably stands for a 1,4-phenylene.

The preferred compounds of the sub-formula Ic encompass those of the sub-formulae Ica to Ico:

$R^1$-Cyc-Cyc-W   Ica $R^1$-Cyc-Thp-W   Icb $R^1$-Cyc-Dio-W   Icc $R^1$-Cyc-Phe-W   Icd $R^1$-Thp-Cyc-W   Ice $R^1$-Dio-Cyc-W   Icf $R^1$-Phe-Cyc-W   Icg $R^1$-Thp-Phe-W   Ich $R^1$-Dio-Phe-W   Ici $R^1$-Phe-Phe-W   Icj $R^1$-Pyr-Phe-W   Ick $R^1$-Thp-Dio-W   Icm $R^1$-Cbl-Cyc-W   Icn $R^1$-Spi-Cyc-W   Ico

Of these, particular preference is given to those of the following sub-formulae:

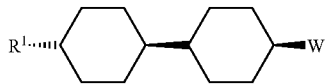

Ica1

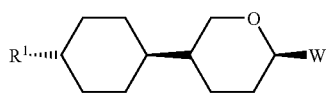

Icb1

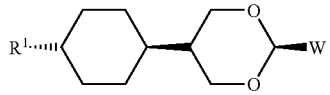

Icc1

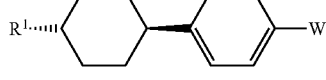

Icd1

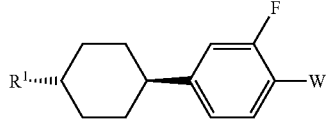

Icd2

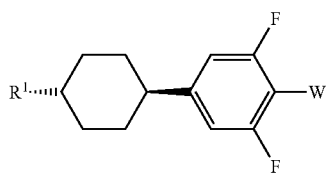

Icd3

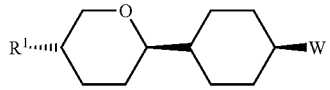

Ice1

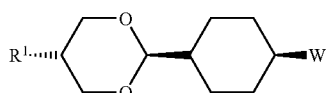

Icf1

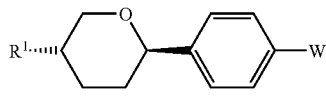

Ich1

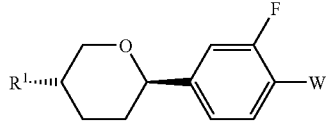

Ich2

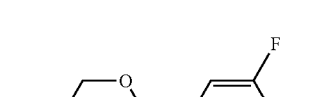

Ich3

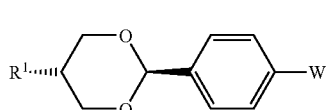

Ici1

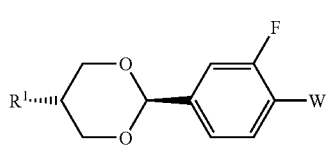

Ici2

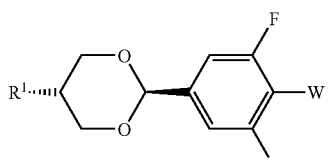
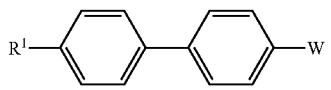
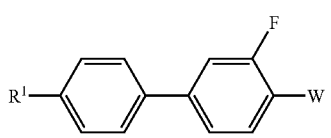
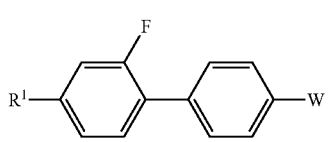
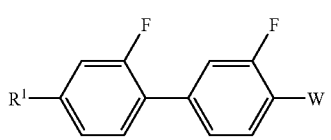
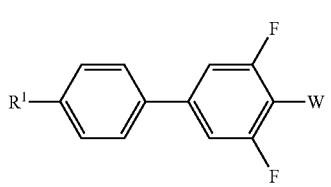
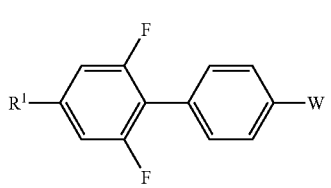
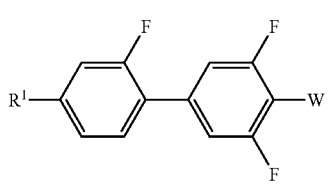
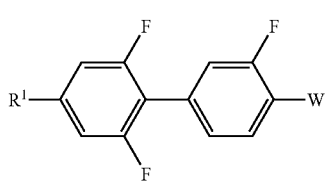
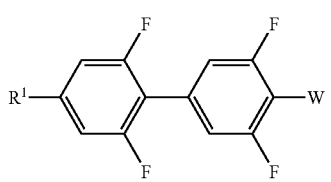

Icj3

Icj1

Icj2

Icj3

Icj4

Icj5

Icj6

Icj7

Icj8

Icj9

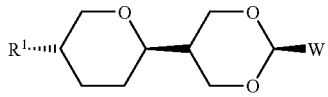 Icm1

 Icn1

Ico1

The preferred compounds of the sub-formula Id encompass those of the sub-formulae Ida to Idp:

| | |
|---|---|
| $R^1$-Cyc-Cyc-$Z^1$—W | Ida |
| $R^1$-Cyc-Thp-$Z^1$—W | Idb |
| $R^1$-Cyc-Dio-$Z^1$—W | Idc |
| $R^1$-Cyc-Phe-$Z^1$—W | Idd |
| $R^1$-Thp-Cyc-$Z^1$—W | Ide |
| $R^1$-Dio-Cyc-$Z^1$—W | Idf |
| $R^1$-Thp-Phe-$Z^1$—W | Idg |
| $R^1$-Dio-Phe-$Z^1$—W | Idh |
| $R^1$-Phe-Phe-$Z^1$—W | Idi |
| $R^1$-Pyr-Phe-$Z^1$—W | Idk |
| $R^1$-Pyd-Phe-$Z^1$—W | Idk |
| $R^1$-Cyc-Phe-$CH_2CH_2$—W | Idm |
| $R^1$-$A^1$-Phe-$CH_2CH_2$—W | Idn |
| $R^1$-Cbl-Cyc-$Z^1$—W | Ido |
| $R^1$-Spi-Cyc-$Z^1$—W | Idp |

The preferred compounds of the sub-formula Ie encompass those of the sub-formulae Iea to Iem:

| | |
|---|---|
| $R^1$-Cyc-$Z^1$-Cyc-W | Iea |
| $R^1$-Thp-$Z^1$-Cyc-W | Ieb |
| $R^1$-$A^1$-$CH_2CH_2$-$A^1$-W | Iec |
| $R^1$-Cyc-$Z^1$-Phe-W | Ied |
| $R^1$-Thp-$Z^1$-Phe-W | Iee |
| $R^1$-$A^1$-OCO-Phe-W | Ief |
| $R^1$-Phe-$Z^1$-Phe-W | Ieg |
| $R^1$-Pyr-$Z^1$-$A^1$-W | Ieh |
| $R^1$-Pyd-$Z^1$-$A^1$-W | Iei |
| $R^1$-Dio-$Z^1$-$A^1$-W | Iej |
| $R^1$-Cbl-$Z^1$-$A^1$-W | Iek |
| $R^1$-Spi-$Z^1$-$A^1$-W | Iem |

Of these, particular preference is given to those of the following sub-formulae:

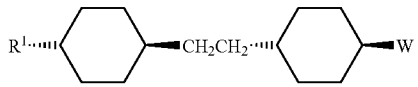
Iea1

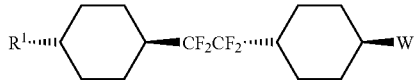
Iea2

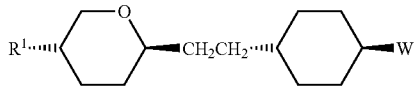
Ieb1

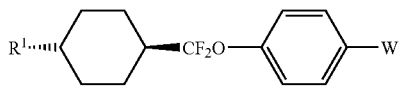
Ied1

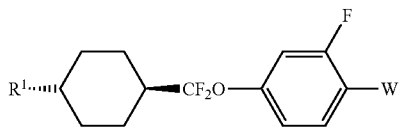
Ied2

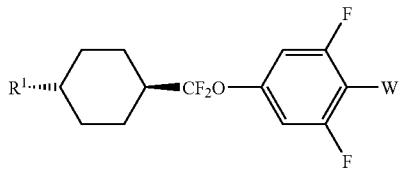
Ied3

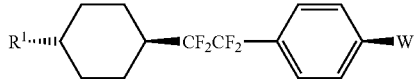
Ied4

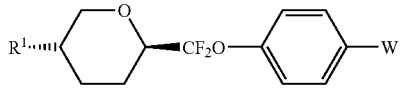
Iee1

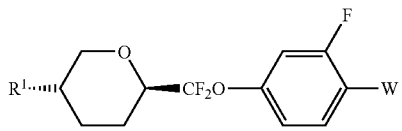
Iee2

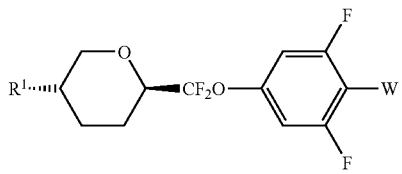
Iee3

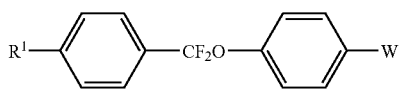
Ieg1

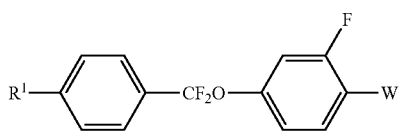
Ieg2

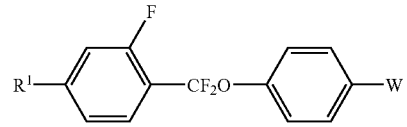
Ieg3

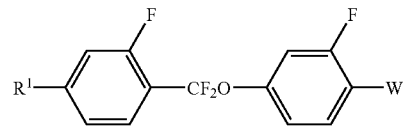
Ieg4

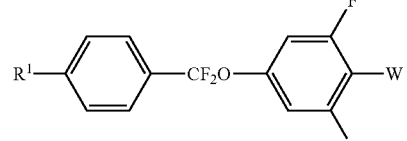
Ieg5

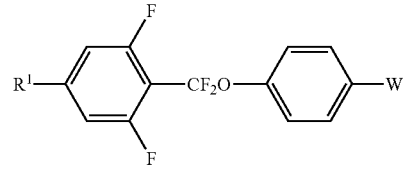
Ieg6

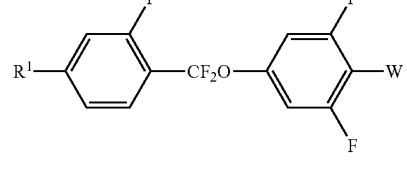
Ieg7

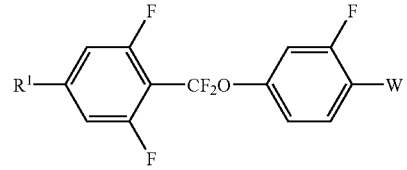
Ieg8

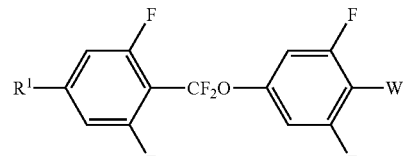
Ieg9

The preferred compounds of the sub-formula if encompass those of the sub-formulae Ifa to Ife:

| | |
|---|---|
| $R^1$-Phe-CH$_2$CH$_2$-A$^1$-Z$^1$—W | Ifa |
| $R^1$-A$^1$-COO-Phe-Z$^1$—W | Ifb |
| $R^1$-Cyc-Z$^1$-Cyc-Z$^1$—W | Ifc |
| $R^1$-Phe-Z$^1$-Phe-Z$^1$—W | Ifd |
| $R^1$-Cyc-CH$_2$CH$_2$-Phe-Z$^1$—W | Ife |

The preferred compounds of the sub-formulae Ig to In encompass those of the sub-formulae Iga to Ima:

| | |
|---|---|
| $R^1$-A$^1$-Cyc-Cyc-W | Iga |
| $R^1$-A$^1$-Cyc-Phe-W | Igb |
| $R^1$-Phe-Phe-Phe-W | Igc |

| | |
|---|---|
| R$^1$-Thp-Dio-Phe-W | Igd |
| R$^1$-Dio-Thp-Phe-W | Ige |
| R$^1$-A$^1$-CH$_2$CH$_2$-A$^1$-Phe-W | Iha |
| R$^1$-Phe-Z$^1$-A$^1$-Phe-W | Ihb |
| R$^1$-A$^1$-Phe-Z$^1$-Phe-W | Iia |
| R$^1$-Cyc-Cyc-Phe-Z$^1$—W | Ija |
| R$^1$-Cyc-Z$^1$-A$^1$-Z$^1$-Phe-W | Ika |
| R$^1$-A$^1$-Z$^1$-Cyc-Phe-Z$^1$—W | Ima |

In the above preferred formulae Ia to 1 h and sub-formulae thereof, R$^1$, A$^1$ Z$^1$ and W generally have the above-mentioned meanings.

In the above preferred formulae Ia to Ih and sub-formulae thereof, R$^1$ preferably denotes a linear alkyl or alkoxy radical having 1 to 7 C atoms or a linear alkenyl or alkenyloxy radical having 2 to 7 C atoms and particularly preferably a linear alkyl radical having 1 to 7 C atoms or a linear alkenyl radical having 2 to 7 C atoms.

In the above preferred formulae Ia to Ih and sub-formulae thereof, Z$^1$ in each case, independently of one another, identically or differently, preferably denotes —CH$_2$CH$_2$—, —C═C—, —C≡C—, —CF$_2$CF$_2$—, —(CO)O—, —O(CO)— or —CF$_2$O—, particularly preferably —CF$_2$O— or —CH$_2$CH$_2$—.

If R$^1$ in the formulae above and below denotes an alkyl radical, this may be straight-chain or branched. It is particularly preferably straight-chain, has 1, 2, 3, 4, 5, 6 or 7 C atoms and accordingly denotes methyl, ethyl, propyl, butyl, pentyl, hexyl or heptyl, furthermore octyl, nonyl, decyl, undecyl, dodecyl, tridecyl, tetradecyl or pentadecyl.

If R$^1$ denotes an alkyl radical in which one CH$_2$ group has been replaced by —O—, this may be straight-chain or branched. It is preferably straight-chain and has 1 to 10 C atoms. The first CH$_2$ group in this alkyl radical has particularly preferably been replaced by —O—, so that the radical R$^1$ acquires the meaning alkoxy and denotes methoxy, ethoxy, propoxy, butoxy, pentyloxy, hexyloxy, heptyloxy, octyloxy or nonyloxy.

Furthermore, a CH$_2$ group elsewhere may also have been replaced by —O—, so that the radical R$^1$ preferably denotes straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R$^1$ denotes an alkyl radical in which one CH$_2$ group has been replaced by —CH═CH—, this may be straight-chain or branched. It is preferably straight-chain and has 2 to 10 C atoms. Accordingly, it denotes vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

Preferred alkenyl groups are C$_2$-C$_7$-1E-alkenyl, C$_4$-C$_7$-3E-alkenyl, C$_5$-C$_7$-4-alkenyl, C$_6$-C$_7$-5-alkenyl and C$_{7-6}$-alkenyl, particularly preferably C$_2$-C$_7$-1E-alkenyl, C$_4$-C$_7$-3E-alkenyl and C$_5$-C$_7$-4-alkenyl.

Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl and 6-heptenyl. Groups having up to 5 carbon atoms are particularly preferred.

If R$^1$ denotes an alkyl radical in which one CH$_2$ group has been replaced by —O— and one has been replaced by —CO—, these are preferably adjacent. These thus contain an acyloxy group —CO—O— or an oxycarbonyl group —O—CO—. These are particularly preferably straight-chain and have 2 to 6 C atoms.

Accordingly, they denote in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)-propyl, 3-(ethoxycarbonyl)propyl or 4-(methoxycarbonyl)butyl.

If R$^1$ denotes an alkyl radical in which one CH$_2$ group has been replaced by unsubstituted or substituted —CH═CH— and an adjacent CH$_2$ group has been replaced by —CO—, —CO—O— or —O—CO—, this may be straight-chain or branched. It is preferably straight-chain and has 4 to 13 C atoms. Accordingly, it particularly preferably denotes acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-meth acryloyloxyethyl, 3-6-methacryloyloxyhexyl, 7-methacryloyloxyheptyl, 8-methacryloyloxyoctyl or 9-methacryloyloxynonyl.

If R$^1$ denotes an alkyl or alkenyl radical which is monosubstituted by CN or CF$_3$, this radical is preferably straight-chain and the substitution by CN or CF$_3$ is in the ω-position.

If R$^1$ denotes an alkyl or alkenyl radical which is at least monosubstituted by halogen, this radical is preferably straight-chain. Halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the co-position.

Compounds of the formula I having a branched wing group R$^1$ may occasionally be of importance owing to better solubility in the conventional liquid-crystalline base materials, but in particular as chiral dopants if they are optically active. Smectic compounds of this type are suitable as component(s) of ferroelectric materials.

Branched groups of this type preferably contain not more than one chain branch. Preferred branched radicals R$^1$ are isopropyl, 2-butyl (=1-methylpropyl), isobutyl (=2-methylpropyl), 2-methylbutyl, isopentyl (=3-methylbutyl), 2-methyl pentyl, 3-methyl pentyl, 2-ethylhexyl, 2-propylpentyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy and 1-methylheptyloxy.

If they are chiral compounds, the formula I and the sub-formulae usually encompass the racemates of these compounds, but also both optically pure components per se and enriched mixtures of these components.

Of the compounds of the formula I and the sub-formulae, preference is given to those in which at least one of the elements R$^1$, n, A$^1$ and Z$^1$ present therein has one of the preferred meanings indicated. Particularly preferred compounds of the formula I arise from corresponding or a plurality of preferred elements.

In the compounds of the formula I, preferred stereoisomers are those in which the rings Cyc and piperidine are trans-1,4-disubstituted. Those of the above-mentioned formulae which contain one or more groups Pyd, Pyr and/or Dio in each case encompass the two 2,5-positional isomers, where the heteroatom is generally preferably located closer to the group W.

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the said reactions. Use can be made here of variants known per se, which are not mentioned here in greater detail.

A further aspect of the invention comprises a process for the preparation of compounds of the formula I which is characterised in that it comprises one or more process steps by means of which a cyclopentane ring is connected in the 5,6-position to a 5,6-dibromo or 5,6-dihydroxy derivative of indane or of benzo-1,3-dioxole. The newly formed cyclopentane ring is substituted in such a way that a substitution corresponding to the respective compounds of the formula I arises directly or after further derivatisation. Further details can be obtained from one or more of the following synthesis schemes and the explanations. The specific substituents indicated which are not reacted directly can of course be varied analogously to the general formula I so long as they do not contain any chemical groups which could be influenced by one of the indicated reactions in a manner apparent to the person skilled in the art.

A synthesis variant of the compounds according to the invention in which X in each case denotes a —CH$_2$— group and Y stands for CF$_3$ is as follows:

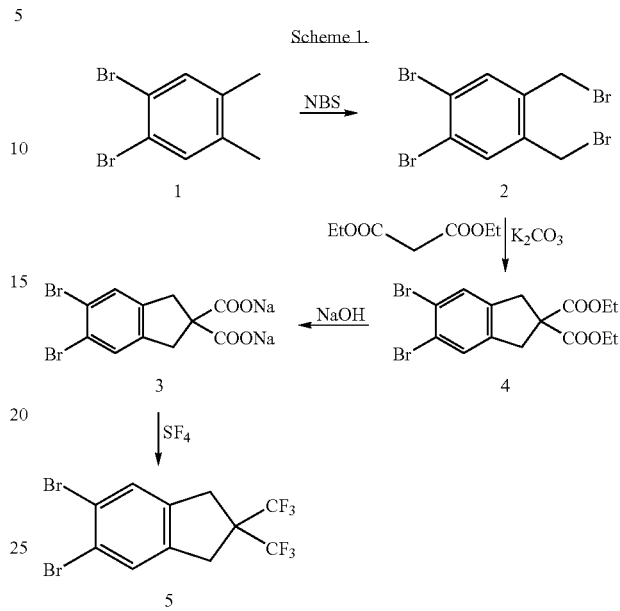

The corresponding compounds according to the invention are obtained from the compound of the formula 5 analogously to Experimental Example 1. To this end, 5 is reacted in accordance with Scheme 2.

The starting materials for the processes shown here or in the examples are either known or can be prepared analogously to known compounds.

The dienodioxoles are prepared analogously to the experimental examples, for example from indanediols in accordance with scheme 3.

Scheme 3.

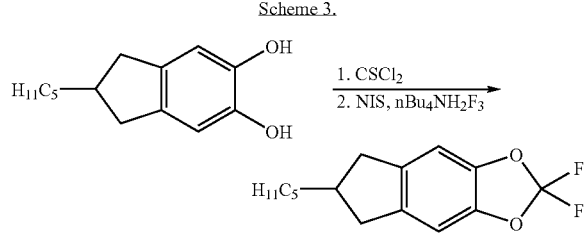

A synthesis variant for the preparation of the indanediols additionally arises from the fluorinated indanes disclosed in DE 4303634 by reaction with sodium methoxide (Scheme 4).

Scheme 4.

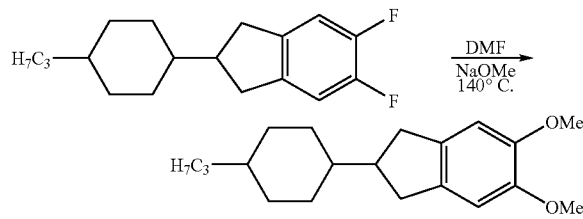

If desired, the starting materials can also be formed in situ by not isolating them from the reaction mixture, but instead immediately converting them further into the compounds of the formula I.

The reactions shown should only be regarded as illustrative. The person skilled in the art will be able to carry out corresponding variants of the syntheses presented and also follow other suitable synthetic routes in order to obtain the compounds of the formula I according to the invention.

The syntheses of various 1,2,3,6,7,8-hexahydro-s-indacene and 6,7-dihydro-5H-indeno[5,6-d]-1,3-dioxole derivatives of the general formula I according to the invention are also described in detail in the examples. The synthesis strategy can be applied to the synthesis of a wide variety of compounds according to the invention through the choice of suitable starting materials. For example, the alkyl chains present can be replaced by various chains and rings in accordance with the formula I. Likewise, rings which are not involved in the reaction can be replaced by other rings and combinations of chains and rings in accordance with formula I.

The liquid-crystalline media according to the invention preferably comprise 2 to 40, particularly preferably 4 to 30, components as further constituents besides one or more compounds according to the invention. In particular, these media comprise 7 to 25 components besides one or more compounds according to the invention. These further constituents are preferably selected from nematic or nematogenic (monotropic or isotropic) substances, in particular substances from the classes of the azoxybenzenes, benzylidene-anilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of the media according to the invention can be characterised by the formulae 1, 2, 3, 4 and 5:

| | |
|---|---|
| R'-L-E-R" | 1 |
| R'-L-(CO)O-E-R" | 2 |
| R'-L-O(CO)-E-R" | 3 |
| R'-L-CH$_2$CH$_2$-E-R" | 4 |
| R'-L-C≡C-E-R" | 5 |

In the formulae 1, 2, 3, 4 and 5, L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe denotes Unsubstituted or fluorine-substituted 1,4-phenylene, Cyc denotes trans-1,4-cyclohexylene or 1,4-cyclohexenylene, Pyr denotes pyrimidine-2,5-diyl or pyridine-2,5-diyl, Dio denotes 1,3-dioxane-2,5-diyl and G denotes 2-(trans-1,4-cyclohexyl)ethyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

R' and/or R" each, independently of one another, denote alkyl, alkenyl, alkoxy, alkoxyalkyl, alkenyloxy or alkanoyloxy having up to 8 C atoms, F, Cl, CN, NCS, —(O)$_i$CH$_{3-k}$F$_k$, where i is 0 or 1 and k is 1, 2 or 3.

In a smaller sub-group of the compounds of the formulae 1, 2, 3, 4 and 5, R' and R" each, independently of one another, denote alkyl, alkenyl, alkoxy, alkoxyalkyl, alkenyloxy or alkanoyloxy having up to 8 C atoms. This smaller sub-group is called group A below, and the compounds are referred to by the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is referred to as group B, R" denotes —F, —Cl, —NCS or —(O)$_i$CH$_{3-k}$F$_k$, where i is 0 or 1 and k is 1, 2 or 3. The compounds in which R" has this meaning are referred to by the sub-formulae 1b, 2b, 3b, 4b and 5b. Particular preference is given to those compounds of the sub-formulae 1b, 2b, 3b, 4b and 5b in which R" has the meaning F, Cl, NCS, CF$_3$, OCHF$_2$ or OCF$_3$.

In the compounds of the sub-formulae 1b, 2b, 3b, 4b and 5b, R' has the meanings indicated in the case of the compounds of the sub-formulae Ia to 5a and is preferably alkyl, alkenyl, alkoxy or alkoxyalkyl.

In a further smaller sub-group of the compounds of the formulae 1, 2, 3, 4 and 5, R" denotes CN. This sub-group is referred to below as group C, and the compounds of this sub-group are correspondingly described by sub-formulae 1c, 2c, 3c, 4c and 5c. In the compounds of the sub-formulae 1c, 2c, 3c, 4c and 5c, R' has the meanings indicated in the case of the compounds of the sub-formulae 1a to 5a and is preferably alkyl, alkoxy or alkenyl.

Besides the preferred compounds of groups A, B and C, other compounds of the formulae 1, 2, 3, 4 and 5 having other variants of the proposed substituents are also customary. All these substances are obtainable by methods which are known from the literature or analogously thereto.

Besides compounds of the formula I according to the invention, the media according to the invention preferably comprise one or more compounds selected from groups A, B and/or C. The proportions by weight of the compounds from these groups in the media according to the invention are preferably:
group A: 0 to 90%, preferably 20 to 90%, particularly preferably 30 to 90%;
group B: 0 to 80%, preferably 10 to 80%, particularly preferably 10 to 65%;
group C: 0 to 80%, preferably 5 to 80%, particularly preferably 5 to 50%;
where the sum of the proportions by weight of the group A, B and/or C compounds present in the respective media according to the invention is preferably 5 to 90% and particularly preferably 10 to 90%.

The media according to the invention preferably comprise 1 to 40%, particularly preferably 5 to 30%, of the compounds according to the invention. Preference is furthermore given to media comprising more than 40%, particularly preferably 45 to 90%, of compounds according to the invention. The media preferably comprise three, four or five compounds according to the invention.

The liquid-crystal mixtures according to the invention are prepared in a manner which is conventional per se. In general, the desired amount of the components used in lesser amount is dissolved in the components making up the principal constituent, preferably at elevated temperature. It is also possible to mix solutions of the components in an organic solvent, for example in acetone, chloroform or methanol, and to remove the solvent again, for example by distillation, after thorough mixing. It is furthermore possible to prepare the mixtures in other conventional manners, for example by using premixes, for example homologue mixtures, or using so-called "multi-bottle" systems.

The dielectrics may also comprise further additives known to the person skilled in the art and described in the literature. For example, 0 to 15%, preferably 0 to 10%, of pleochroic dyes and/or chiral dopants can be added. The individual compounds added are employed in concentrations of 0.01 to 6%, preferably 0.1 to 3%. However, the concentration data of the other constituents of the liquid-crystal mixtures, i.e. the liquid-crystalline or mesogenic compounds, are indicated without taking into account the concentration of these additives.

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n and m C atoms respectively; n and m are integers and preferably denote 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nN.F.F | $C_nH_{2n+1}$ | CN | F | F |
| nF | $C_nH_{2n+1}$ | F | H | H |
| nF.F | $C_nH_{2n+1}$ | F | H | F |
| nF.F.F | $C_nH_{2n+1}$ | F | F | F |
| nOF | $OC_nH_{2n+1}$ | F | H | H |
| nCl | $C_nH_{2n+1}$ | Cl | H | H |
| nCl.F | $C_nH_{2n+1}$ | Cl | H | F |
| nCl.F.F | $C_nH_{2n+1}$ | Cl | F | F |
| nCF$_3$ | $C_nH_{2n+1}$ | CF$_3$ | H | H |
| nCF$_3$.F | $C_nH_{2n+1}$ | CF$_3$ | H | F |
| nCF$_3$.F.F | $C_nH_{2n+1}$ | CF$_3$ | F | F |
| nOCF$_3$ | $C_nH_{2n+1}$ | OCF$_3$ | H | H |
| nOCF$_3$.F | $C_nH_{2n+1}$ | OCF$_3$ | H | F |
| nOCF$_3$.F.F | $C_nH_{2n+1}$ | OCF$_3$ | F | F |
| nOCF$_2$ | $C_nH_{2n+1}$ | OCHF$_2$ | H | H |
| nOCF$_2$.F | $C_nH_{2n+1}$ | OCHF$_2$ | H | F |
| nOCF$_2$.F.F | $C_nH_{2n+1}$ | OCHF$_2$ | F | F |
| nS | $C_nH_{2n+1}$ | NCS | H | H |
| nS.F | $C_nH_{2n+1}$ | NCS | H | F |
| nS.F.F | $C_nH_{2n+1}$ | NCS | F | F |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | $COOC_mH_{2m+1}$ | H | H |

TABLE A

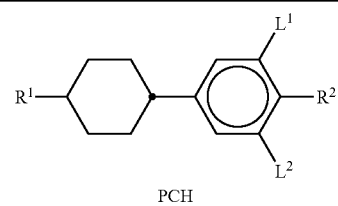

PCH

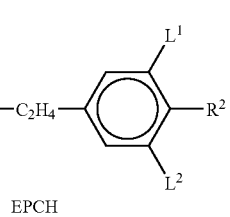

EPCH

TABLE A-continued
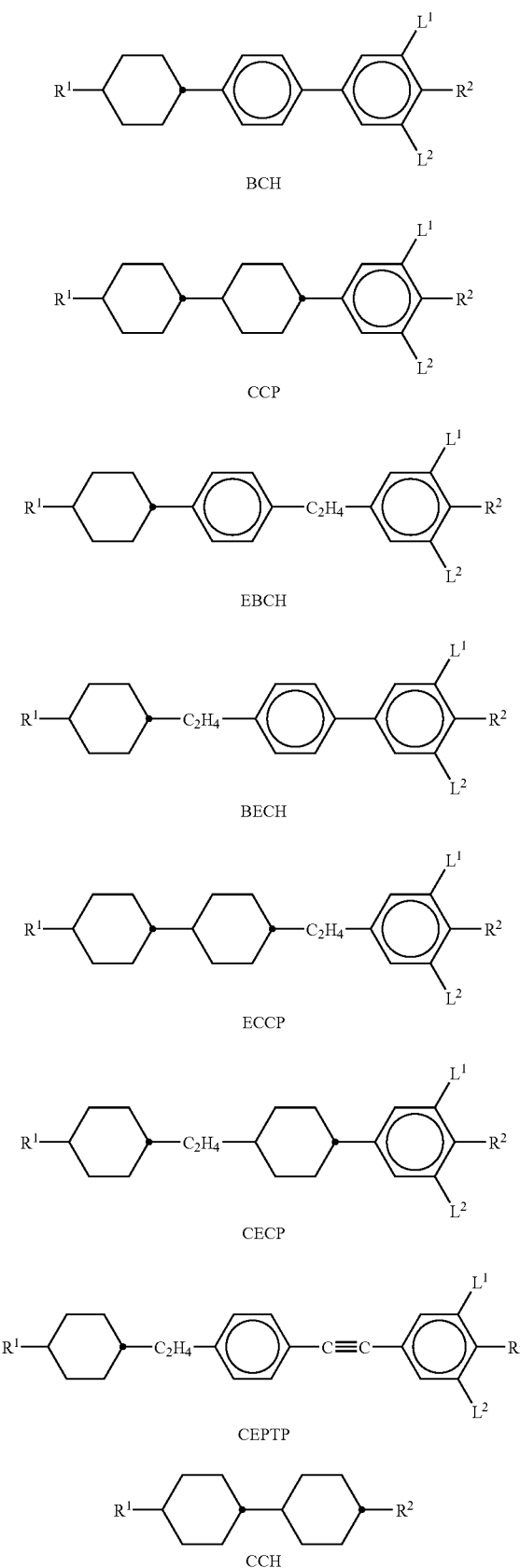
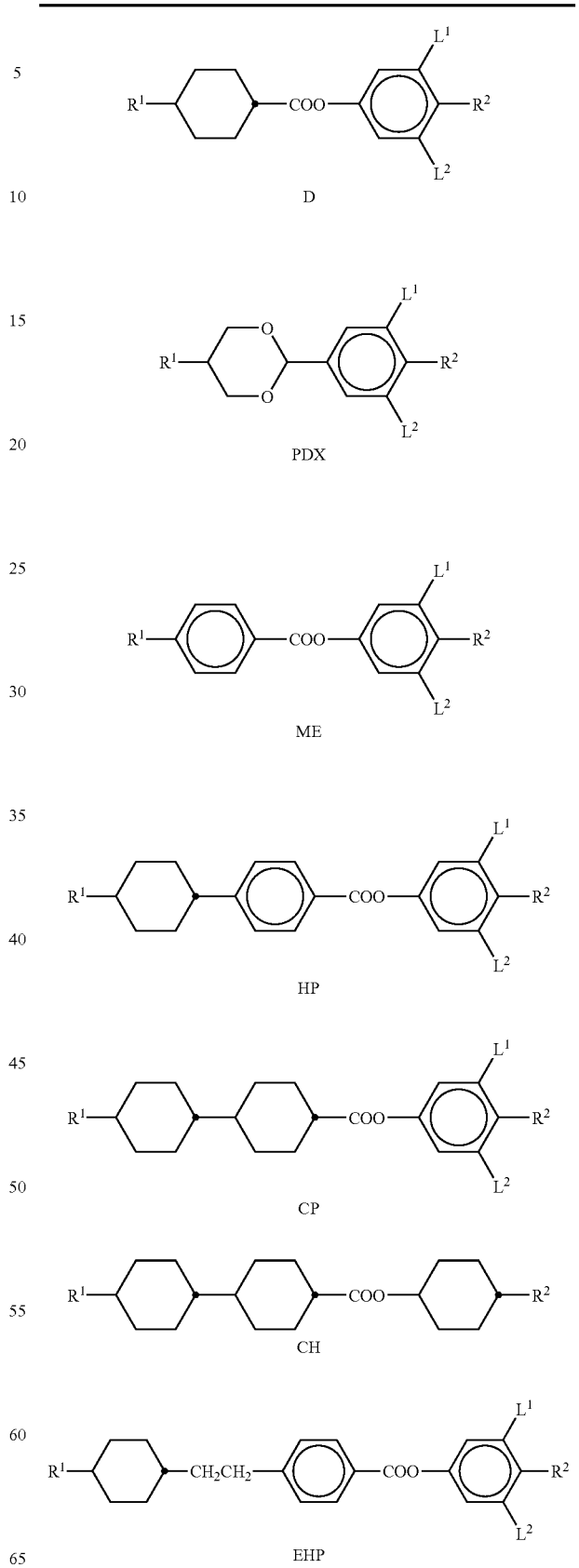

TABLE B
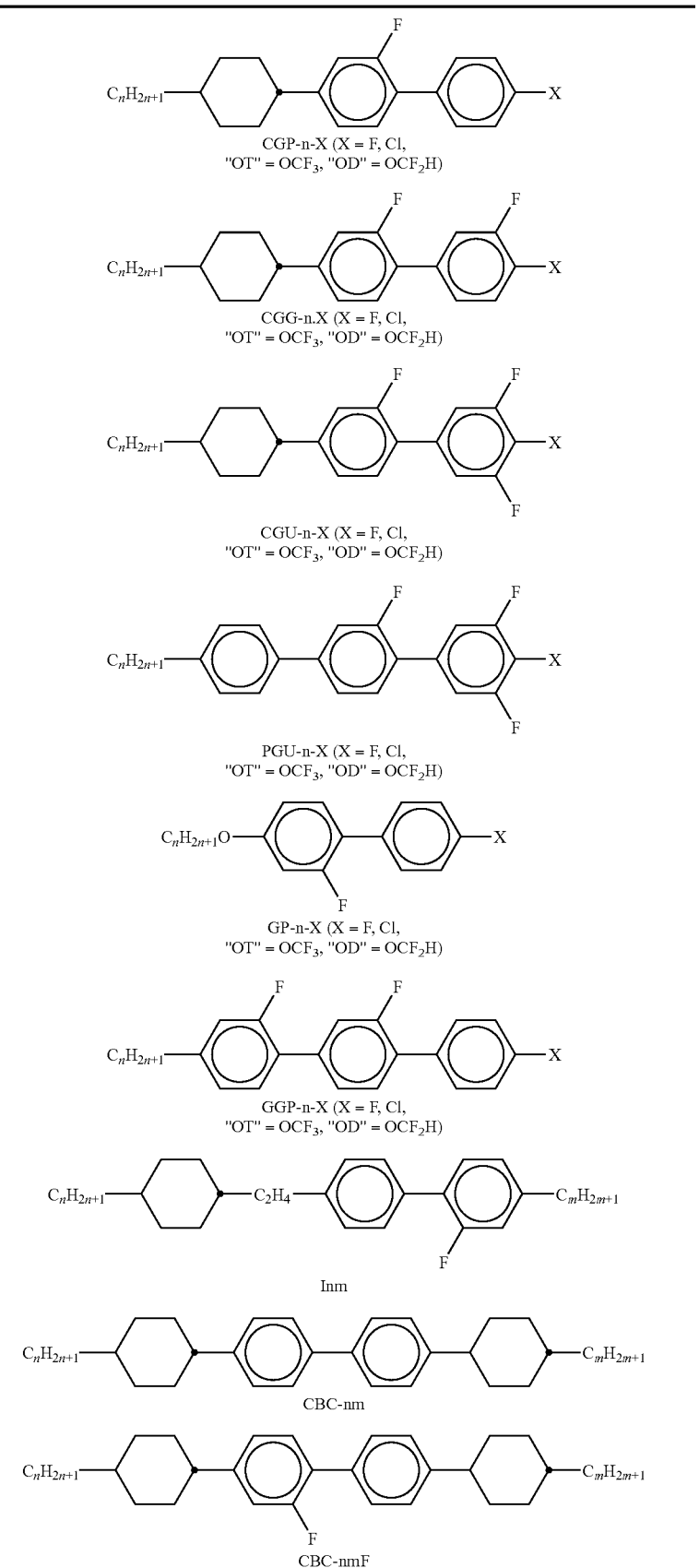

TABLE B-continued
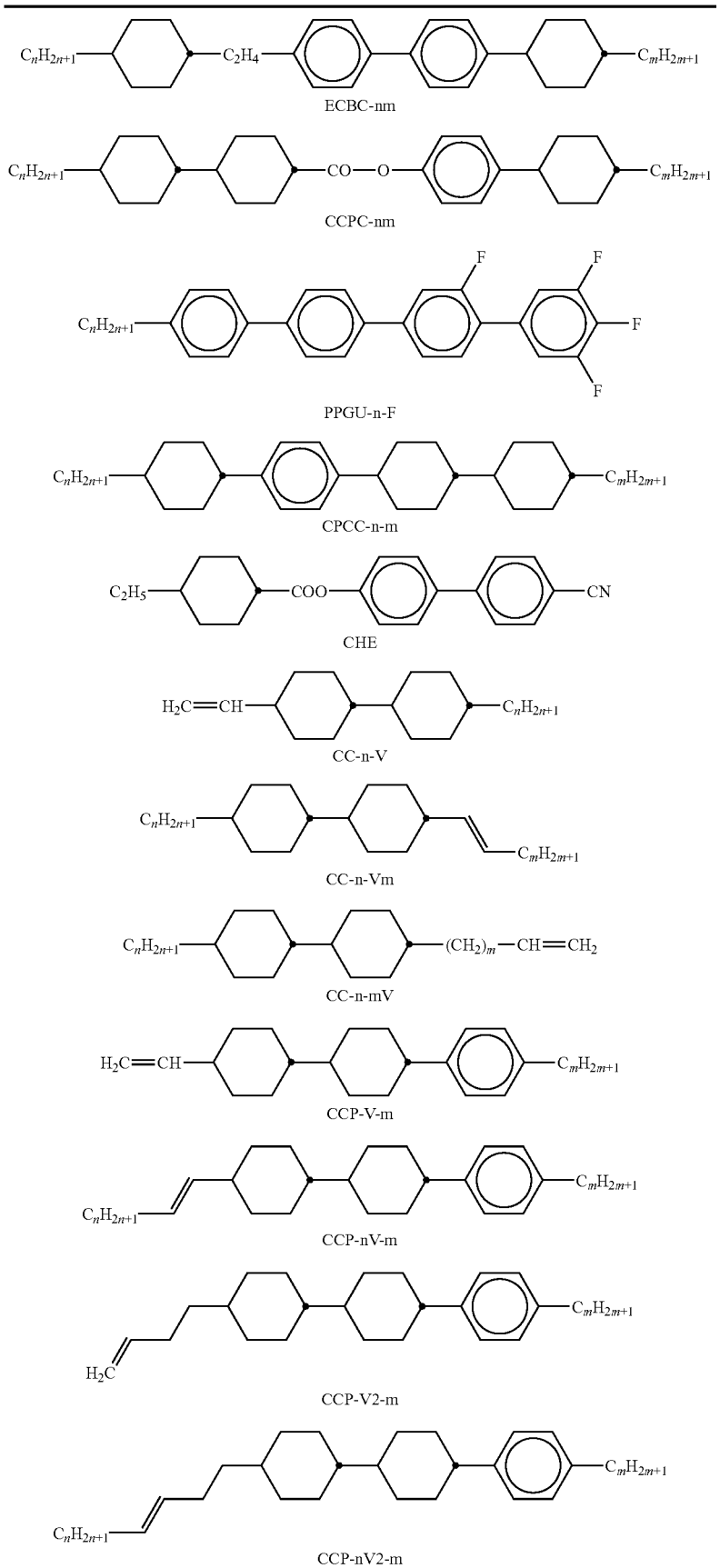

TABLE B-continued
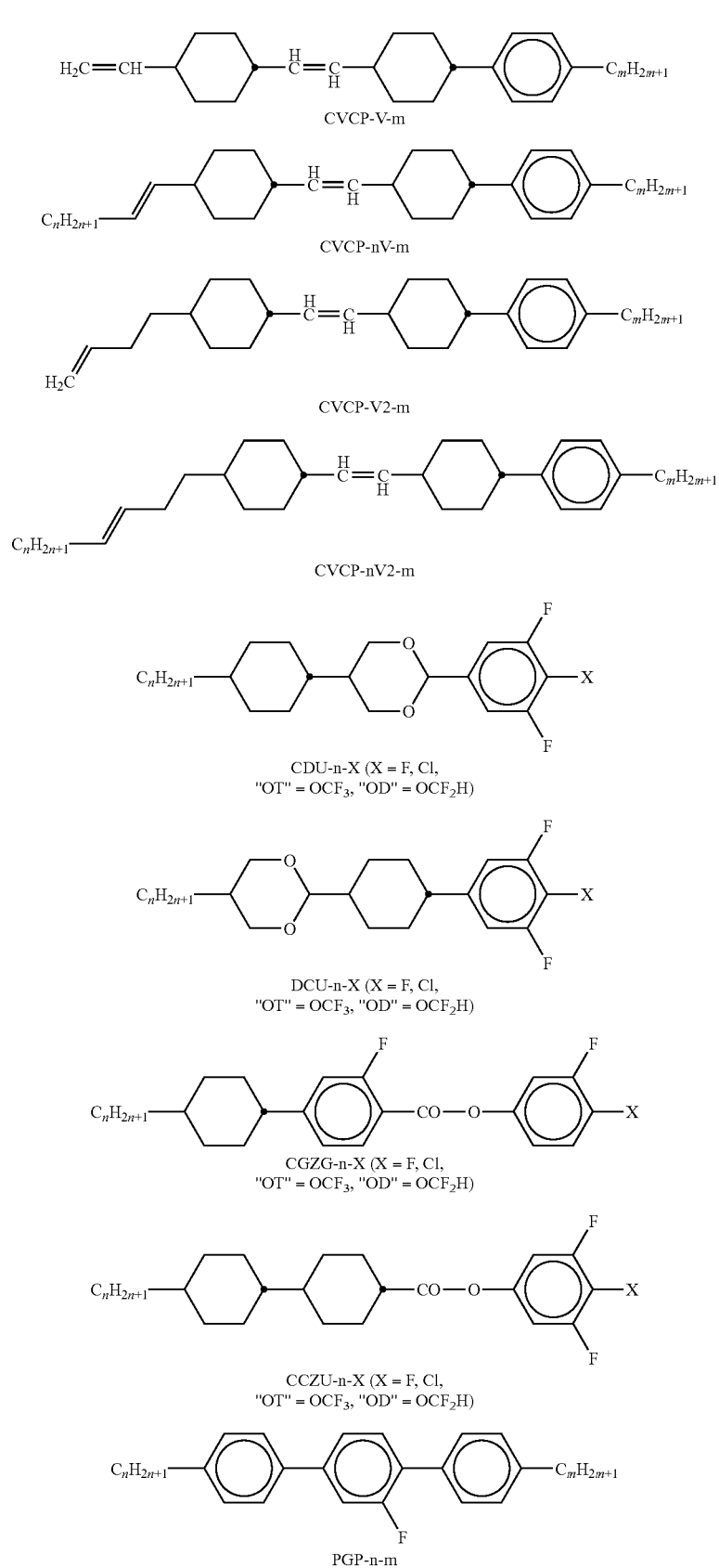

TABLE B-continued
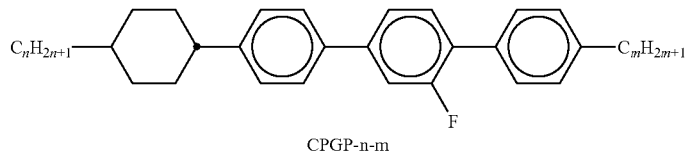
CPGP-n-m
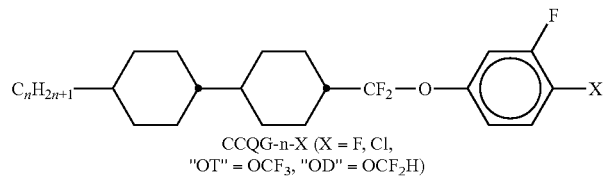
CCQG-n-X (X = F, Cl,
"OT" = OCF$_3$, "OD" = OCF$_2$H)
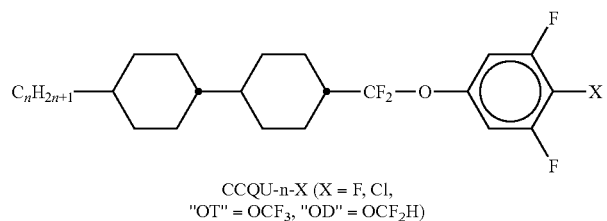
CCQU-n-X (X = F, Cl,
"OT" = OCF$_3$, "OD" = OCF$_2$H)
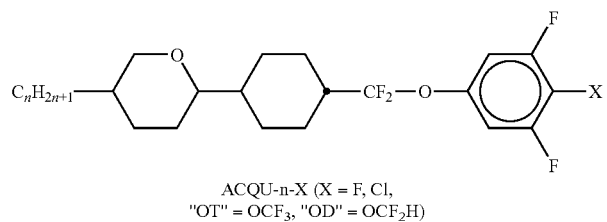
ACQU-n-X (X = F, Cl,
"OT" = OCF$_3$, "OD" = OCF$_2$H)
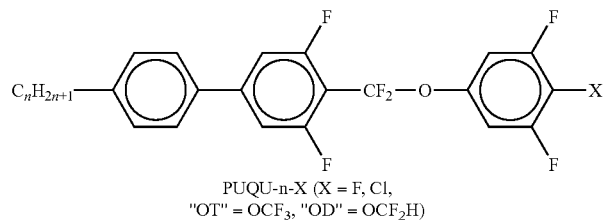
PUQU-n-X (X = F, Cl,
"OT" = OCF$_3$, "OD" = OCF$_2$H)
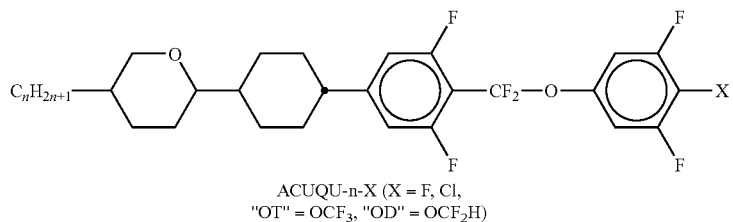
ACUQU-n-X (X = F, Cl,
"OT" = OCF$_3$, "OD" = OCF$_2$H)
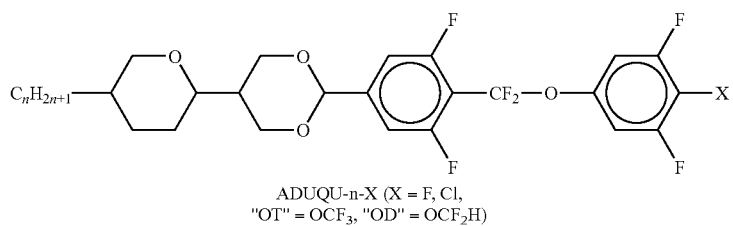
ADUQU-n-X (X = F, Cl,
"OT" = OCF$_3$, "OD" = OCF$_2$H)

TABLE B-continued

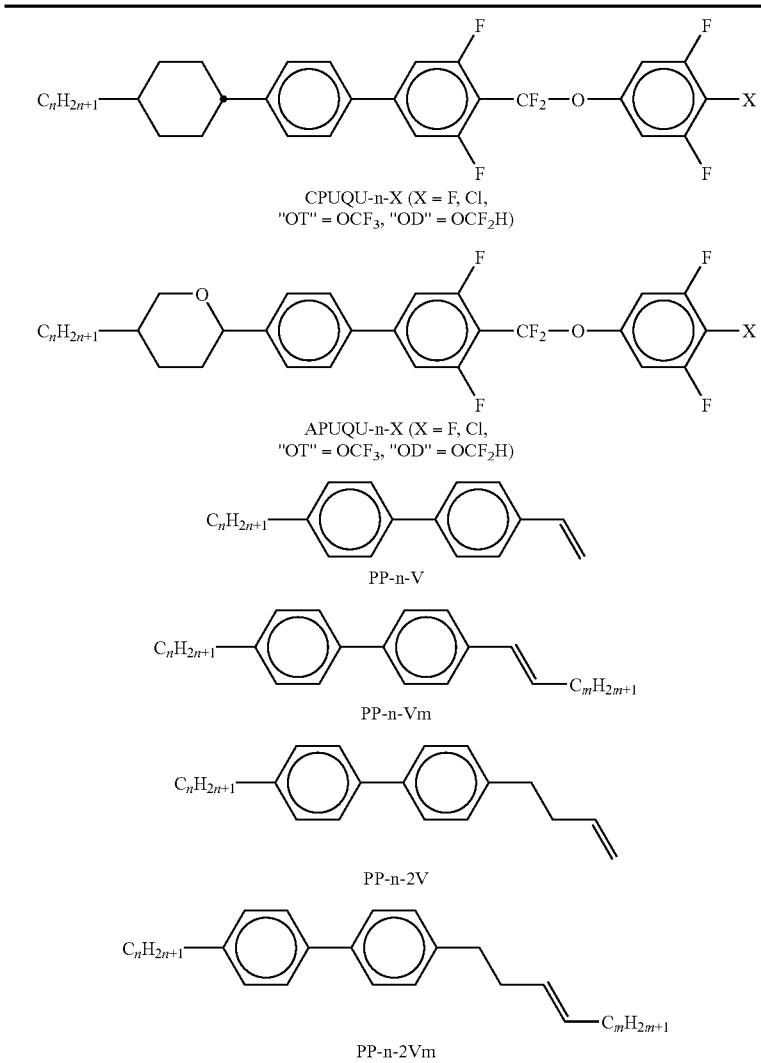

The liquid-crystalline media according to the invention preferably comprise:

- seven or more, preferably eight or more compounds, preferably having a different basic structure, selected from the group of compounds in Tables A and B;
- one or more, preferably two or more, particularly preferably three or more compounds, preferably having a different basic structure, selected from the group of compounds in Table A;
- three or more, preferably four or more, particularly preferably five or more compounds, preferably having a different basic structure, selected from the group of compounds in Table B.

Table C

Table C shows possible dopants which are generally added to the mixtures according to the invention. The mixtures preferably comprise 0-10% by weight, in particular 0.01-5% by weight and particularly preferably 0.01-3% by weight, of dopants.

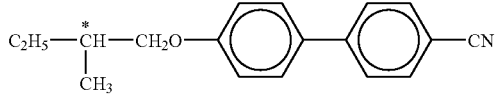

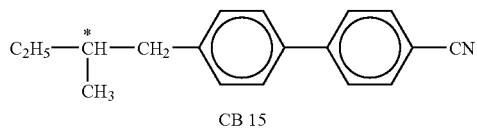

-continued
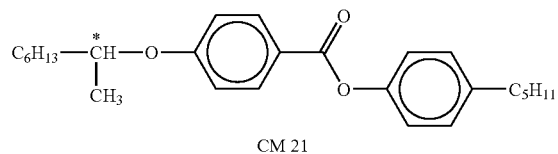
CM 21
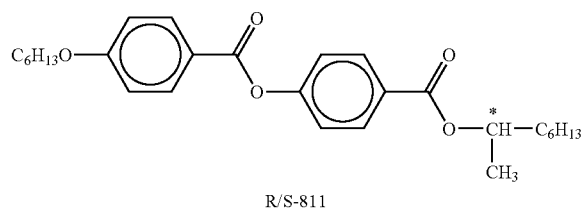
R/S-811
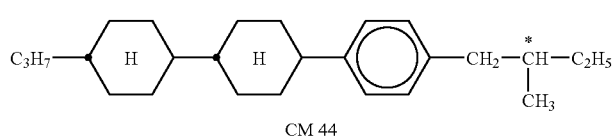
CM 44
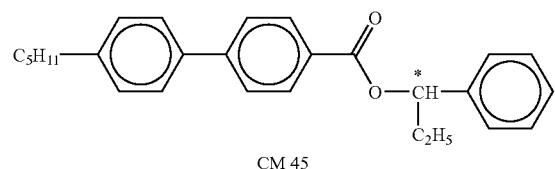
CM 45
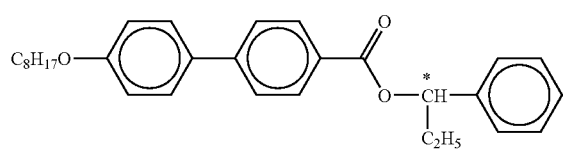
CM 47
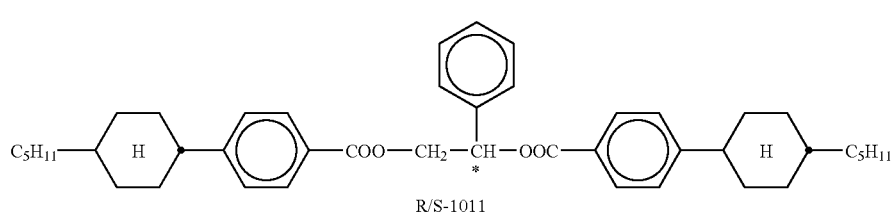
R/S-1011
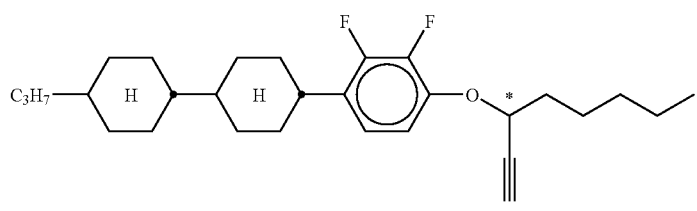
R/S-3011
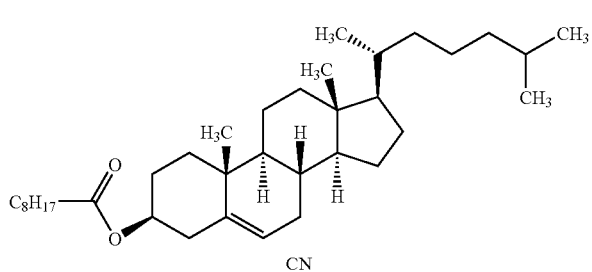
CN

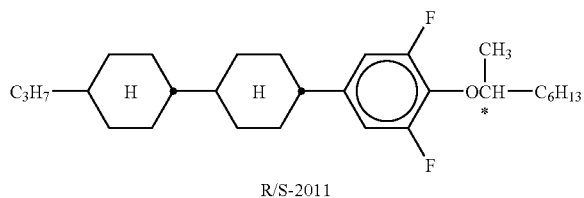
R/S-2011
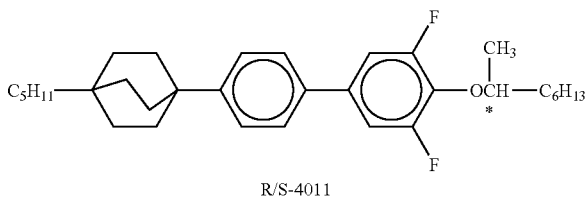
R/S-4011
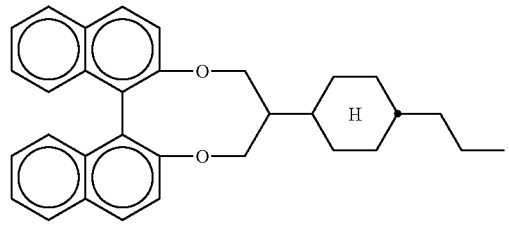
R/S-5011
Table D
Stabilisers which can be added, for example, to the mixtures according to the invention are indicated below.
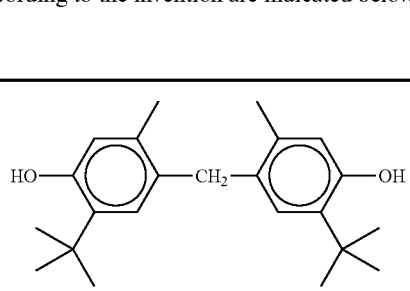
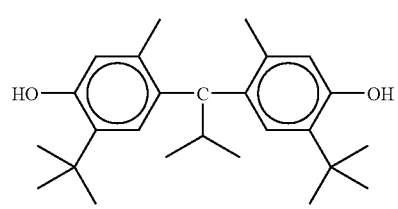
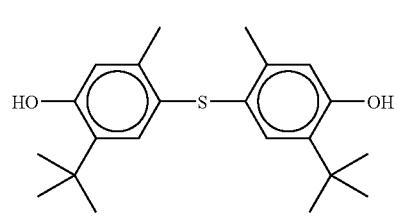
-continued
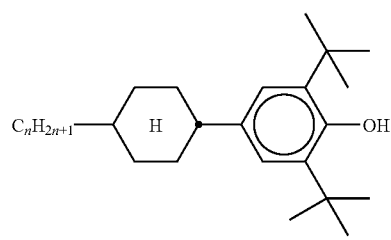
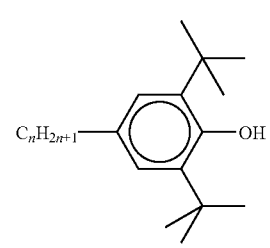
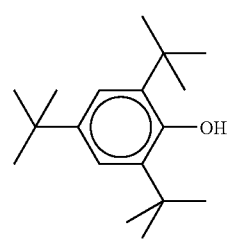

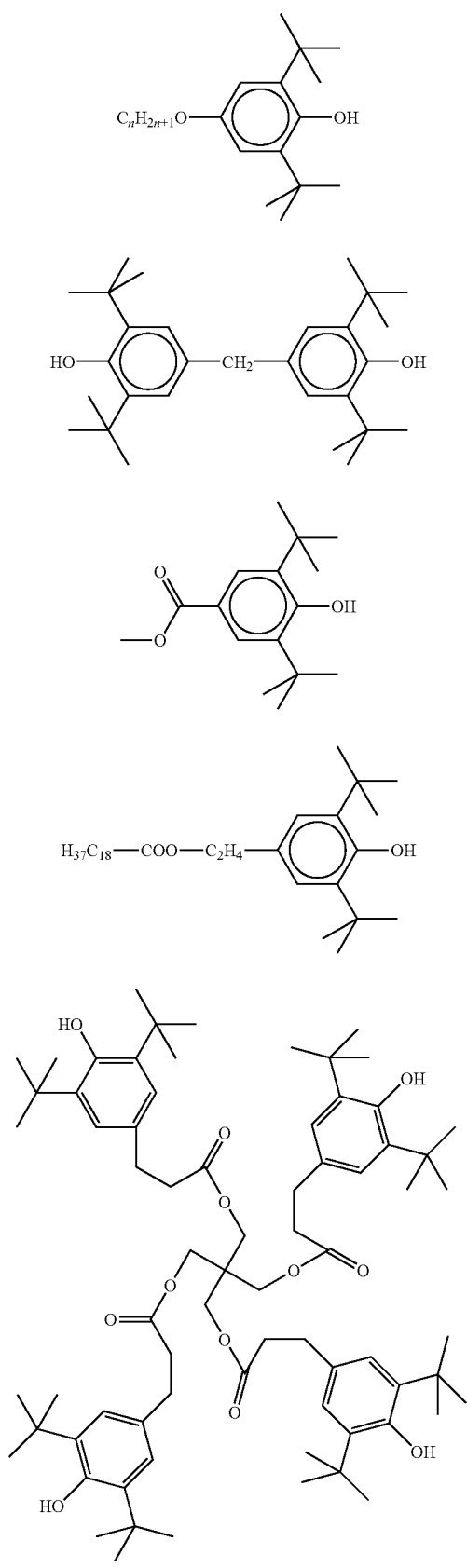
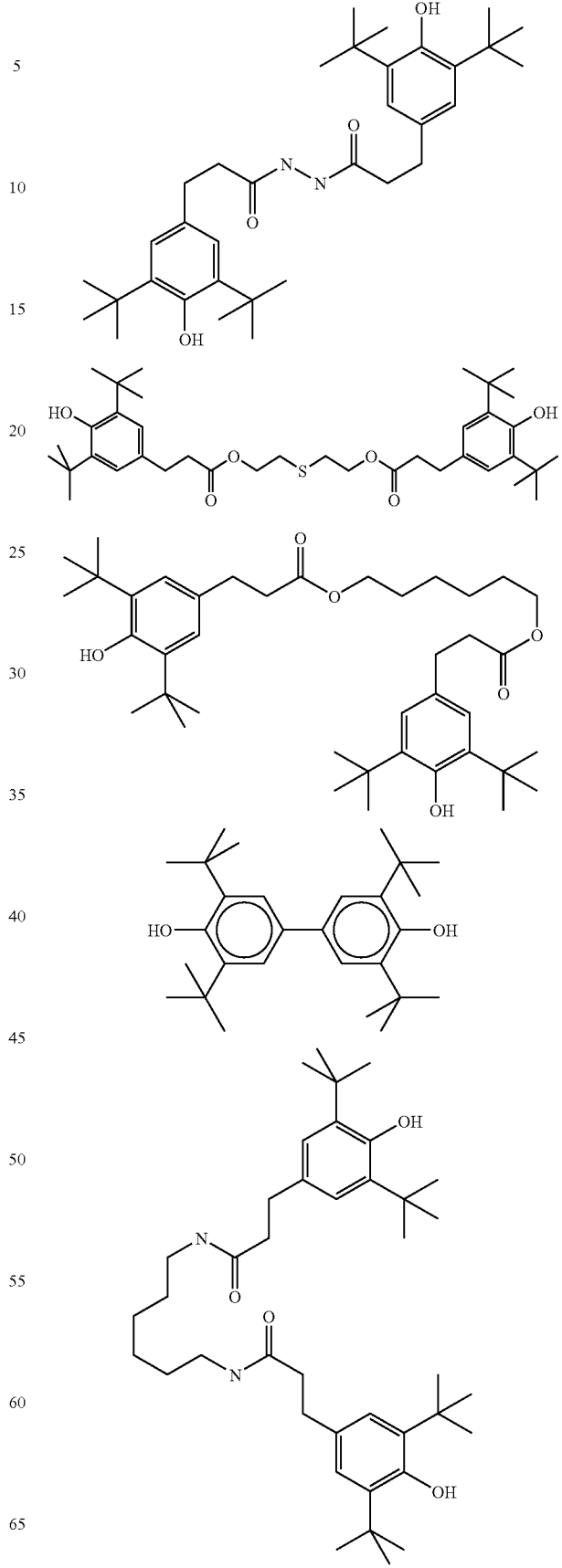

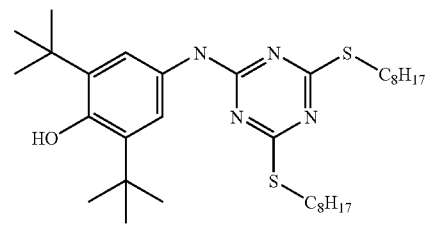
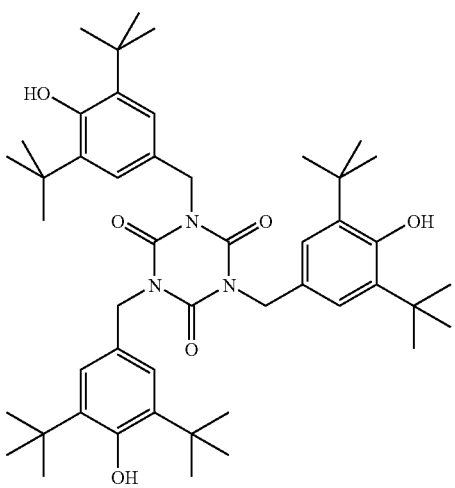
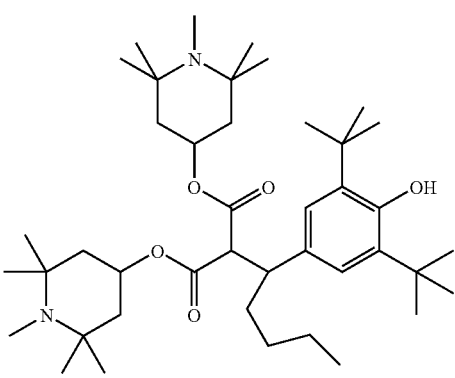
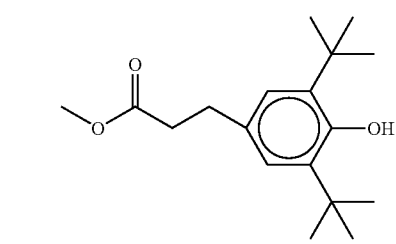
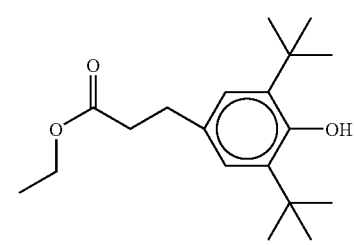
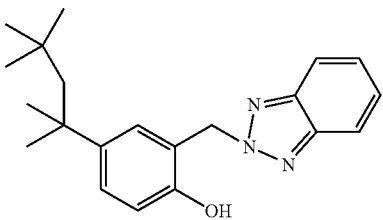
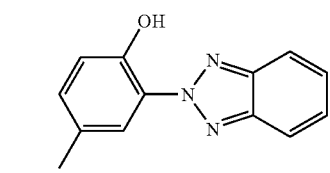
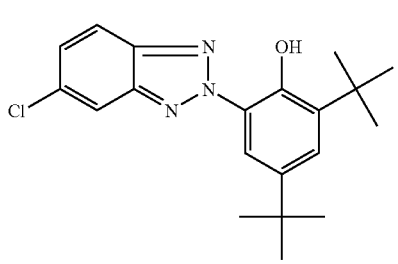
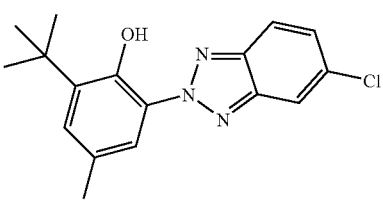
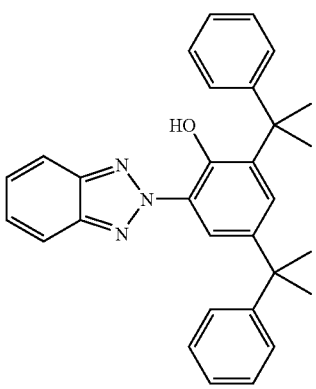
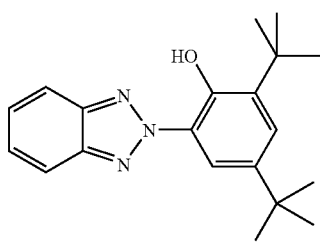

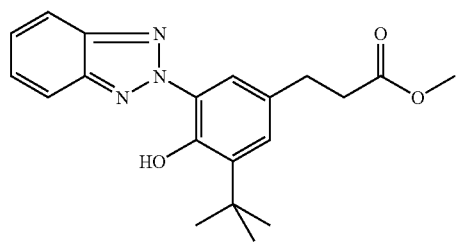

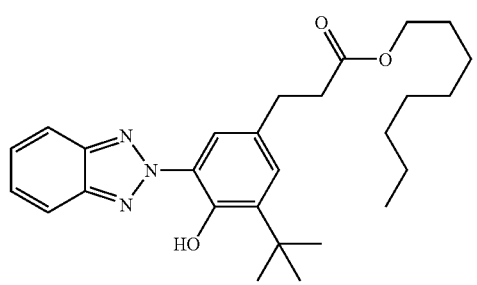

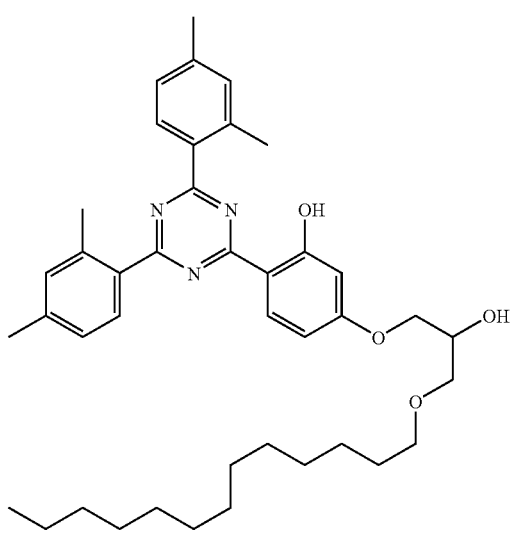

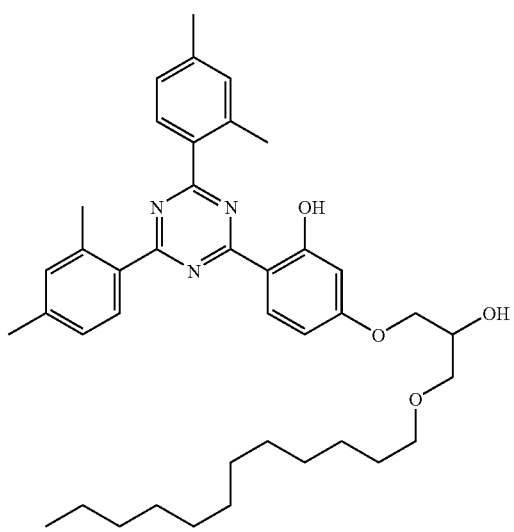

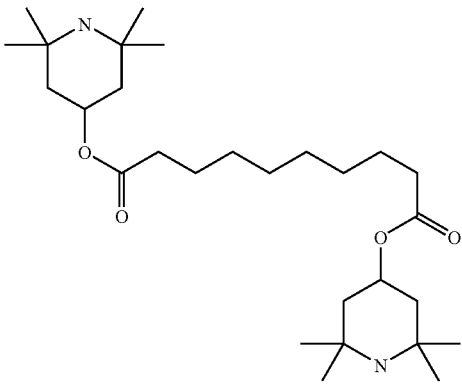

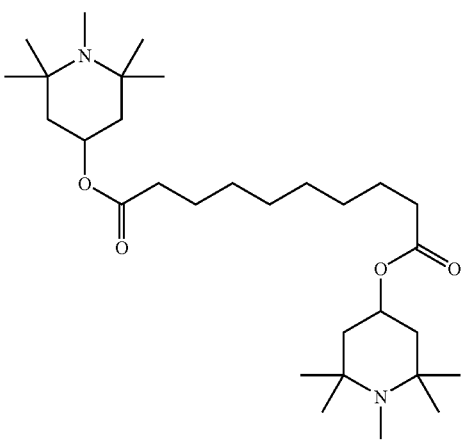

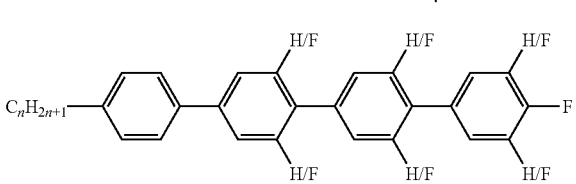

The following examples explain the invention without intending to restrict it.

Above and below, the following abbreviations are used
RT room temperature
THF tetrahydrofuran
MTB ether methyl tert-butyl ether
Py pyridine
BuLi n-butyllithium
TLC thin-layer chromatography
in vac. under reduced pressure
DMF dimethylformamide
NIS N-iodosuccinimide
DMPU N,N'-dimethyl-N,N'-propyleneurea

EXAMPLES

Example 1

The synthesis building block 2 can be prepared by the procedures of M. Kuroboshi, T. Hiyama *Synlett* (1994), 251-252 and E. L. Stogryn *J. Org. Chem.* (1972), 37, 673. The starting material 3 can be prepared as described by F. Huet, M. Pellet, A. Lechevalier, J.-M. Conia, *J. Chem. Res. Miniprint* (1982), 9, 2528-2578.

Reaction step 1.1

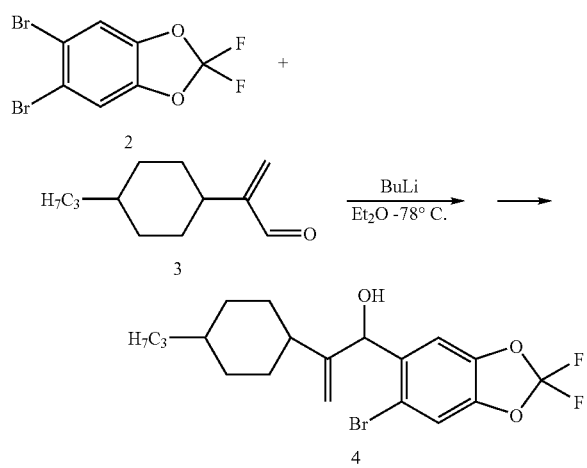

50.0 g (158 mmol) of the dibromophenyl compound 2 are dissolved in 200 ml of diethyl ether under nitrogen, and 100 ml of a 15% solution of BuLi in n-hexane are added at −70° C., and the mixture is held at this temperature for 1 h. 29.0 g (161 mmol) of the unsaturated aldehyde 3 are subsequently added to the batch. After stirring overnight at RT, the batch is hydrolysed. The aqueous phase is extracted with MTB ether, and the organic phase is dried over sodium sulfate, evaporated and purified on silica gel.

Reaction step 1.2

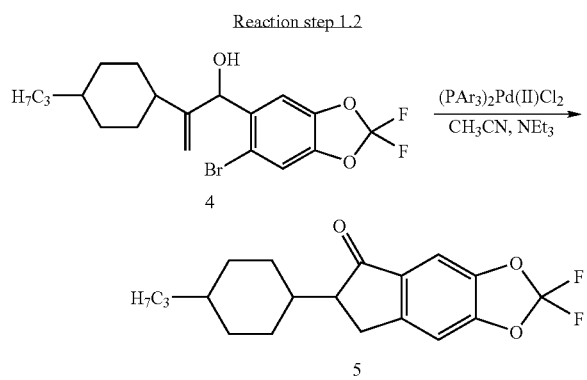

25.0 g (60.0 mmol) of the allyl alcohol 4, 4.3 g of bis(tri-o-tolylphosphine)palladium dichloride and 25 ml of triethylamine are dissolved in 180 ml of acetonitrile, and the mixture is refluxed for 4 h until the allyl alcohol has completely reacted. The cooled batch is added to water, extracted with MTB ether, dried over sodium sulfate, evaporated and purified on silica gel.

Reaction step 1.3

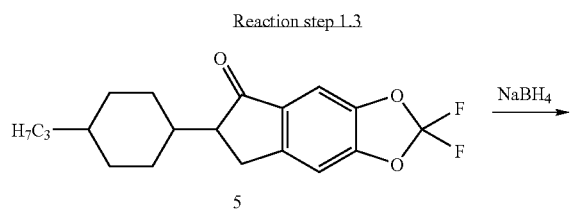

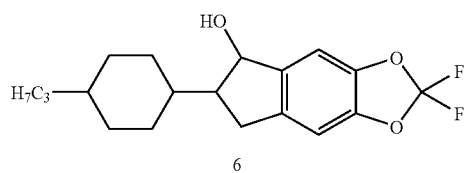

25.0 g (74.3 mmol) of the indanone 5 are dissolved in 150 ml of ethanol, and 5.7 g (155 mmol) of sodium borohydride are added in portions. After completion of the reaction (TLC), the batch is hydrolysed, the ethanol is removed under reduced pressure, and the residue is taken up in water and extracted with MTB ether. After evaporation, the product 6 is employed in the next step without further purification.

Reaction step 1.4

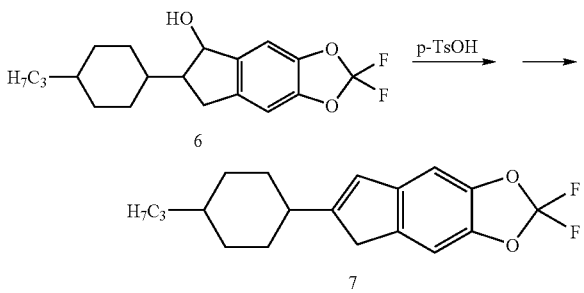

15.0 g (44.3 mmol) of the indanol 6 are dissolved in 150 ml of toluene together with 500 mg of p-toluenesulfonic acid monohydrate, and the mixture is refluxed on a water separator. The batch is subsequently washed with sat. sodium hydrogencarbonate solution, dried over sodium sulfate, evaporated and purified on silica gel.

Reaction step 1.5

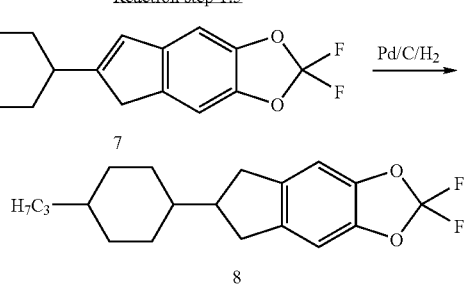

10.0 g (31.2 mmol) of the indene 7 are dissolved in 50 ml of THF and hydrogenated for 9 h at RT under a hydrogen pressure of 10 bar on a palladium catalyst (5% Pd/C). The catalyst is subsequently separated off, the hydrogenation solution is evaporated, and the residue is purified on silica gel.

Example 2

The preparation of the indane derivative 10 from the corresponding dibromobenzyl bromide 9 is carried out analogously to WO 94/18285.

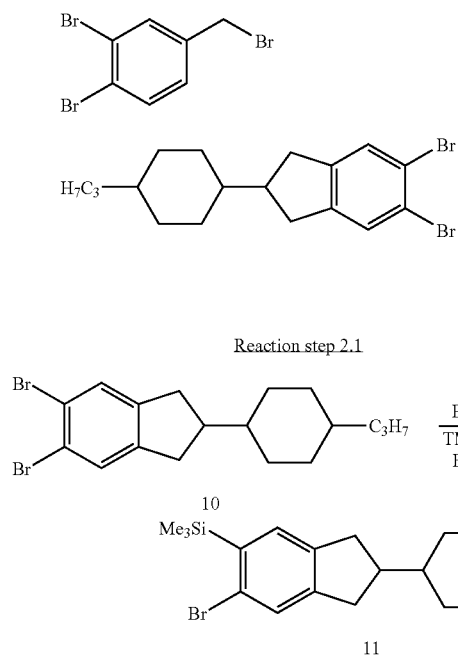

Reaction step 2.1

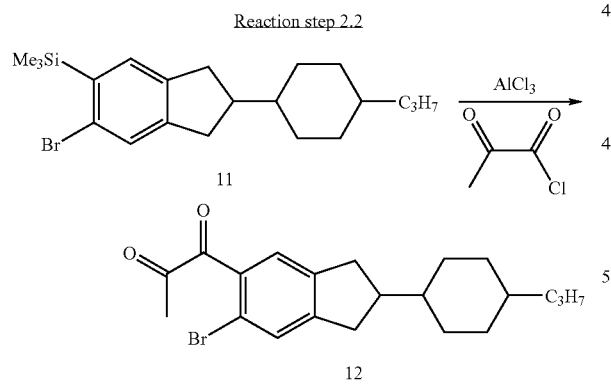

50.0 g (125 mmol) of the indane 10 are dissolved in 200 ml of diethyl ether under nitrogen, and 78.5 ml of a 15% solution of BuLi in n-hexane are added at −70° C., and the mixture is held at this temperature for 1 h. 16.5 ml (130 mmol) of trimethylsilyl chloride are subsequently added to the batch. After stirring overnight at RT, the batch is hydrolysed. The aqueous phase is extracted with MTB ether, and the organic phase is dried over sodium sulfate, evaporated and purified on silica gel.

Reaction step 2.2

8.0 g (75.1 mmol) of 2-oxopropionyl chloride in 40 ml of cyclohexane are initially introduced under nitrogen, and a solution of 30.0 g (76.2 mmol) of the silyl compound 11 in 20 ml of cyclohexane is added at 2-3° C. 10.7 g (80.0 mmol) of aluminium chloride are subsequently introduced into the batch in portions at −2 to +2° C. After removal of the cooling, the reaction mixture warms to 50° C. and is held at this temperature until the reaction subsides. The batch is added to ice-water and extracted with MTB ether. The organic phase is dried over sodium sulfate, evaporated and purified on silica gel.

Reaction step 2.3

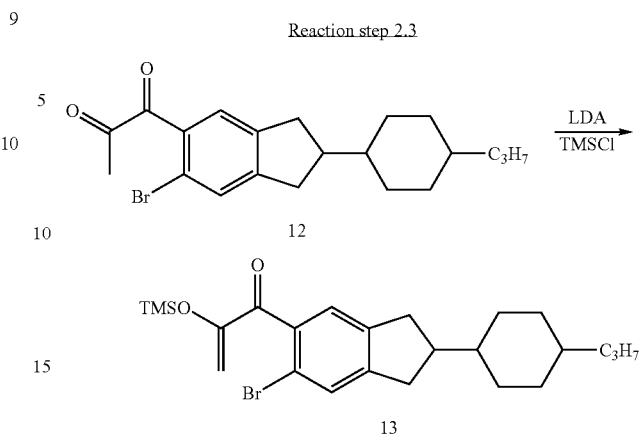

35.0 g (89.5 mmol) of the indane 12 are dissolved in 150 ml of THF under nitrogen, and 46.4 ml of a 26% solution of lithium diisopropylamide (LDA) in cyclohexane/ethylbenzene/THF are added at −70° C., and the mixture is held at this temperature for 1 h. 12.0 ml (95.0 mmol) of trimethylsilyl chloride (TMSCl) are subsequently added to the batch. After stirring overnight at RT, the batch is hydrolysed. The aqueous phase is extracted with MTB ether, and the organic phase is dried over sodium sulfate, evaporated and purified on silica gel.

Reaction step 2.4

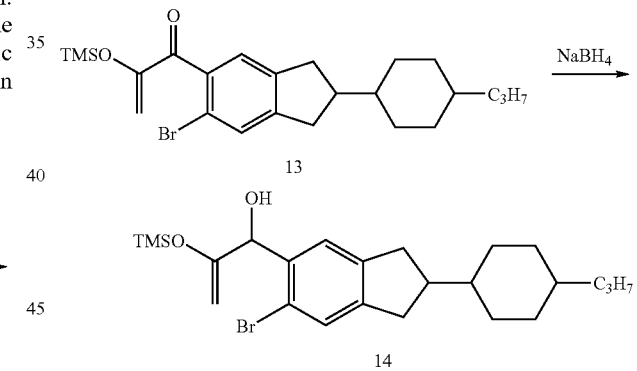

25.0 g (54.0 mmol) of the ketone 13 are dissolved in 250 ml of ethanol, and 4.2 g (113 mmol) of sodium borohydride are added in portions. After completion of the reaction (TLC), the batch is hydrolysed, the ethanol is removed under reduced pressure, and the residue is taken up in water and extracted with MTB ether. After evaporation, the product is employed in the next step without further purification.

Reaction step 2.5

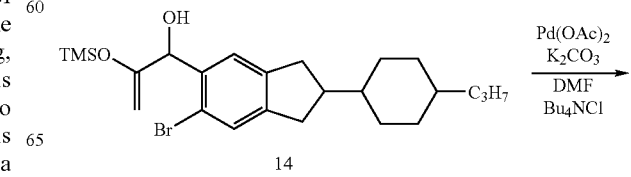

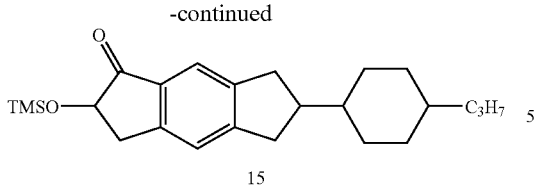

15

10.8 g (36.5 mmol) of tetrabutylammonium chloride monohydrate, 9.4 g (67.6 mmol) of $K_2CO_3$ and 379 mg (1.7 mmol) of palladium(II) acetate are added under nitrogen to a solution of 17.0 g (36.5 mmol) of the silylenol ether 14 in 150 ml of DMF, and the mixture is warmed to 80° C. After completion of the reaction, the cooled batch is added to 1000 ml of sat. sodium chloride solution and extracted with MTB ether. After drying over sodium sulfate and evaporation of the organic phase, the residue obtained is purified on silica gel.

Reaction step 2.6

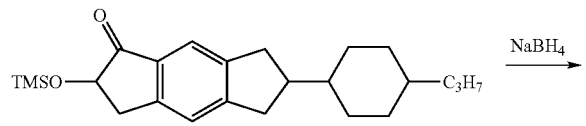

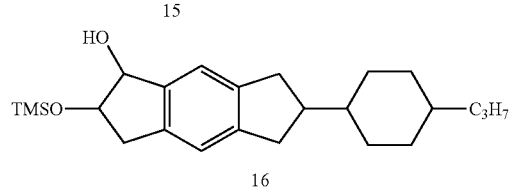

16

22.0 g (57.2 mmol) of the indanone 15 are dissolved in 150 ml of ethanol, and 4.2 g (113 mmol) of sodium borohydride are added in portions. After completion of the reaction (TLC), the batch is hydrolysed, the ethanol is removed under reduced pressure, and the residue is taken up in water and extracted with MTB ether. After evaporation, the product 16 is employed in the next step without further purification.

Reaction step 2.7

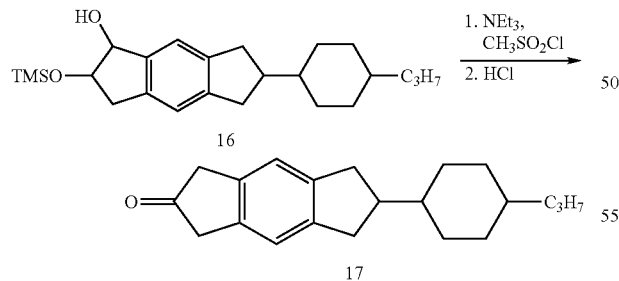

10.0 g (25.9 mmol) of the indanol, 16.8 ml of triethylamine and 60 mg of 4-(dimethylamino)pyridine (DMAP) are dissolved under nitrogen, and 2.2 ml (28.4 mmol) of methanesulfonyl chloride are added at 10-15° C., and the mixture is subsequently refluxed for 5 h. The cooled batch is washed with water and sat. sodium chloride solution and evaporated. The residue obtained is taken up in THF, and 1 ml of conc. hydrochloric acid is added. After 3 h, the reaction mixture is added to sat. sodium chloride solution and extracted with MTB ether. The organic phase is evaporated and purified on silica gel.

Reaction step 2.8

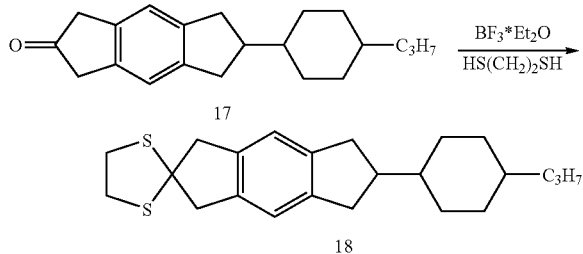

19 ml of boron trifluoride/diethyl ether complex are added at −15 to −10° C. under nitrogen to a solution of 8.0 g (27.0 mmol) of the indanone 17 and 5.5 ml (65.6 mmol) of ethanedithiol in 65 ml of dichloromethane. The batch thaws overnight and is added to sat. sodium hydrogencarbonate solution and stirred until the evolution of gas is complete. The aqueous phase is extracted with DCM and evaporated. The residue is purified on silica gel.

Reaction step 2.9

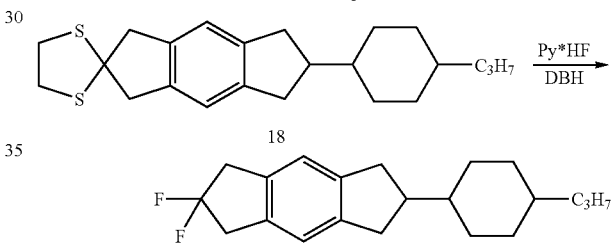

A solution of 8.0 g (21.5 mmol) of the dithiolane 18 in 30 ml of dichloromethane is added at −75° C. to a suspension of 25.1 g (86.9 mmol) of 1,3-dibromo-5,5-dimethylhydantoin (DBH) in 65 ml of dichloromethane and 25 ml of a 65% solution of hydrogen fluoride in pyridine. After 3 h, the batch is slowly warmed to 0° C. and added to 750 ml of ice-cold 2N sodium hydroxide solution to which 60 ml of 39% sodium hydrogensulfite solution have been added. The pH is adjusted to 8, and the aqueous phase is extracted with methylene chloride. The organic phase is dried over sodium sulfate, evaporated and purified on silica gel.

Example 3

Reaction step 3.1

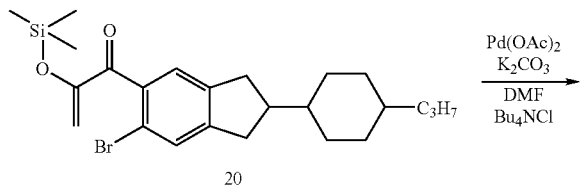

-continued

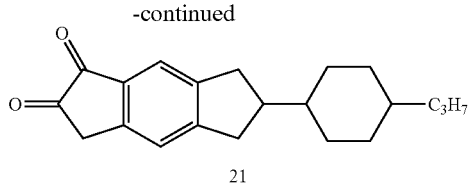
21

9.6 g (32.4 mmol) of tetrabutylammonium chloride monohydrate, 8.3 g (60.0 mmol) of $K_2CO_3$ and 336 mg (1.5 mmol) of palladium(II) acetate are added under nitrogen to a solution of 15.0 g (32.4 mmol) of the silylenol ether 20 in 150 ml of DMF, and the mixture is warmed to 80° C. After completion of the reaction, the cooled batch is added to 1000 ml of sat. sodium chloride solution and extracted with MTB ether. The organic phase is evaporated, the residue obtained is taken up in THF, and 1 ml of conc. hydrochloric acid is added. After 2 h, the batch is added to sat. sodium chloride solution and extracted with MTB ether. After drying over sodium sulfate and evaporation of the organic phase, the residue obtained is purified on silica gel.

Reaction step 3.2

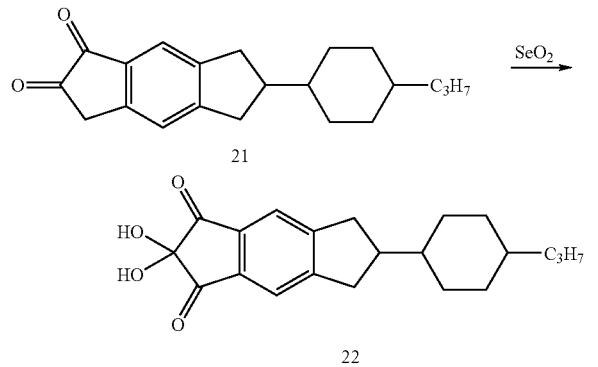

10.0 g (90.2 mmol) of selenium dioxide are dissolved in 250 ml of a dioxane/water mixture (240:10) with warming. 13.0 g (41.9 mmol) of the diketone 21 in dioxane are added to the cooled solution, and the mixture is heated at the boil overnight. The deposited selenium is separated off, and the solution is added to ice-water. After extraction with MTB ether, the organic phase is dried over sodium sulfate and evaporated. The residue is purified on silica gel.

Reaction step 3.3

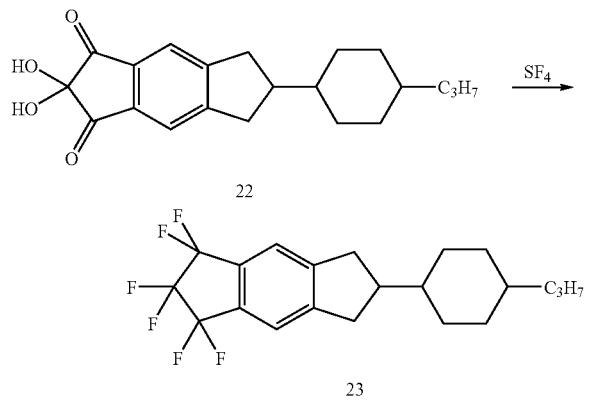

10.0 g (29.2 mmol) of the hydrate 22 are brought to reaction with 19.5 g (180 mmol) of sulfur tetrafluoride at 120° C. The crude reaction product is taken up in dichloromethane, washed with water, evaporated and purified on silica gel.

Example 4

The ketal 24 of hexafluoroacetone is prepared by the method of R. Mietchen, D. Rentsch, Tetrahedron (1992), 48(39), 8393-8400 and used to synthesise the compound 25 analogously to Example 1.

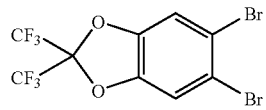
24

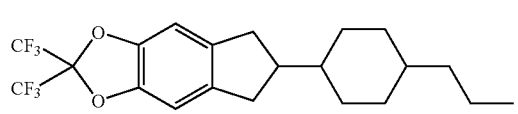
25

Example 5

Reaction step 5.1

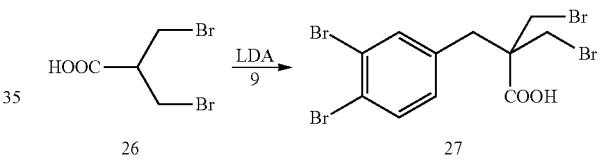
26    27

129 ml (250 mmol) of a 26% solution of lithium diisopropylamide in cyclohexane/ethylbenzene/THF are added at −70° C. under nitrogen to a solution of 30.0 g (122 mmol) of the carboxylic acid 26 and 46.0 g (140 mmol) of the benzyl bromide 9 (cf. Example 2) in 300 ml of THF, and the mixture is held at low temperature for 3 h. After thawing overnight, the batch is added to water and acidified using semi-conc. HCl. The aqueous phase is extracted with MTB ether. The organic phase is washed with sat. sodium chloride solution, dried over sodium sulfate and purified on silica gel.

Reaction step 5.2

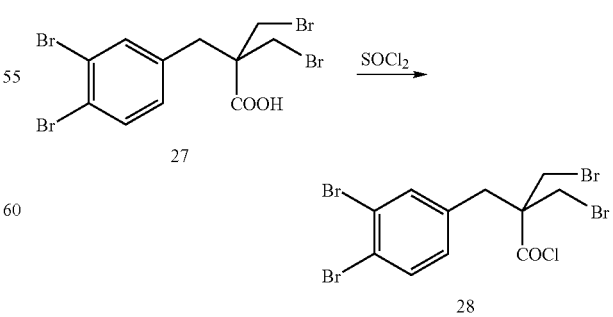
27

28

10 ml (138 mmol) of thionyl chloride and one drop of DMF are added to 25.0 g of the carboxylic acid 27. When the evolution of gas has subsided, the batch is warmed at 90° C. for 1 h. Excess thionyl chloride is subsequently distilled off, and the residue obtained is employed in the subsequent step without further purification.

Reaction step 5.3

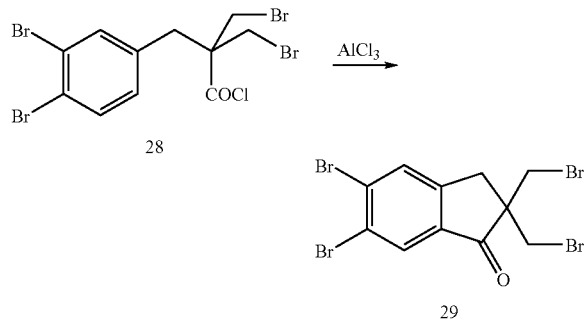

A solution of the acid chloride (23.0 g crude) in 25 ml of dichloromethane is slowly added at −20° C. under nitrogen to a suspension of 6.1 g (45.6 mmol) of aluminium chloride in 50 ml of dichloromethane, and the mixture is stirred at this temperature for 4 h. The batch is hydrolysed using ice. Water is subsequently added until a solution is formed. The aqueous phase is extracted with dichloromethane, and the organic phase is dried, evaporated and passed over silica gel.

Reaction step 5.4

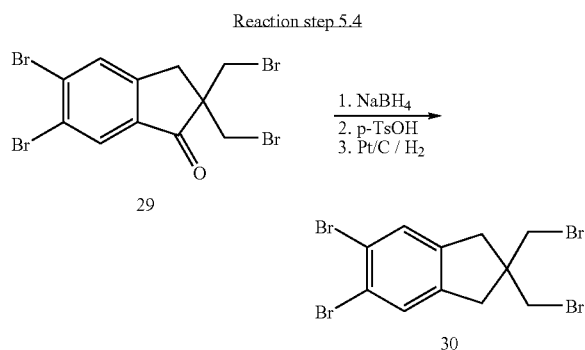

15.0 g (31.5 mmol) of the indanone 29 are dissolved in 50 ml of ethanol, and 2.3 g (60.0 mmol) of sodium borohydride are added in portions. After completion of the reaction (TLC), the batch is hydrolysed, the ethanol is removed under reduced pressure, and the residue is taken up in water and extracted with MTB ether. After evaporation, the product is dissolved in 100 ml of toluene, p-toluenesulfonic acid is added, and the mixture is heated at the boil on a water separator. The cooled batch is washed with sat. sodium hydrogencarbonate solution and evaporated. The residue obtained is filtered through a thin layer of silica gel (toluene). The crude material now isolated is dissolved in THF and hydrogenated on a platinum catalyst. The hydrogenation solution is evaporated, and the residue is purified over silica gel.

Reaction step 5.5

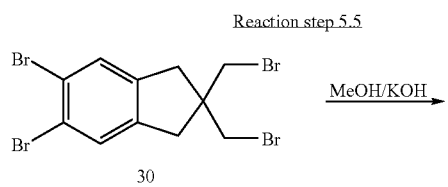

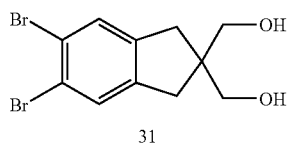

60 ml of methanolic potassium hydroxide solution are added to 9.00 g (19.5 mmol) of the tetrabromide 30, and the mixture is heated at the boil. After completion of the reaction (TLC), the methanol is removed, and the residue is diluted with water and acidified. The aqueous phase is extracted with MTB ether. The organic phase is dried over sodium sulfate and evaporated. The residue obtained is purified on silica gel.

Reaction step 5.6

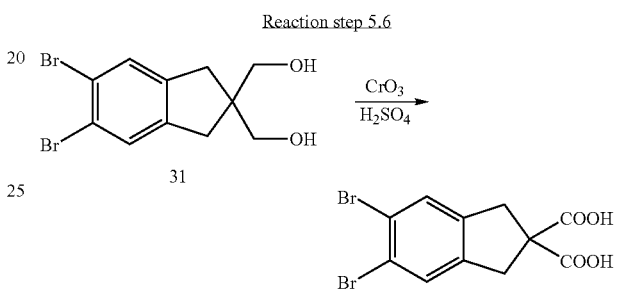

5.00 g (14.9 mmol) of the diol 31 are dissolved in 25 ml of acetone, and 8.1 ml of Jones reagent are added at a temperature of below 30° C. The brown coloration of the batch which occurs during the addition is repeatedly reversed by dropwise addition of conc. sulfuric acid. When the addition is complete, the cooling is removed, and the batch is stirred overnight at room temperature. The batch is added to 150 ml of water and extracted with MTB ether. The organic phase is washed with sat. sodium chloride solution, dried over sodium sulfate and evaporated. The residue is recrystallised from isopropanol.

Reaction step 5.7

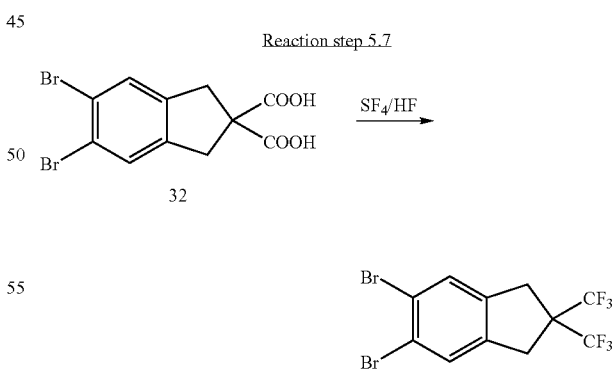

36.4 g (100 mmol) of the dicarboxylic acid 32 are brought to reaction at 40° C. with 20.0 g (1.0 mop of hydrogen fluoride and 70.0 g (650 mmol) of sulfur tetrafluoride for 24 h. Potassium hydroxide solution is added to the batch, which is extracted with n-pentane. The organic phase is evaporated, and the residue obtained is purified on silica gel.

The compound 34 is prepared from the indane 33 analogously to Example 1.

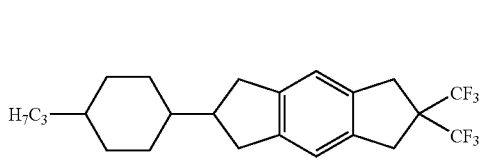

Example 6

Reaction step 6.1

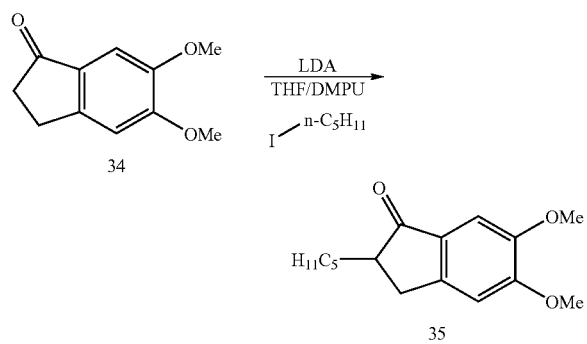

45 ml (90 mmol) of a 2M solution of lithium diisopropylamide in THF/ethylbenzene are diluted at 0° C. with 100 ml of each of THF and DMPU, and a suspension of 17.5 g (90 mmol) of the indanone 34 in THF is subsequently added in portions at −70° C. After 1 h, 11.5 ml (90 mmol) of iodopentane are added. The batch is stirred for 18 h at RT, subsequently added to water and acidified. The aqueous phase is extracted with n-heptane. The organic phase is washed with sat. hydrogen carbonate solution and evaporated. The residue is employed in the subsequent step without further purification.

Reaction step 6.2

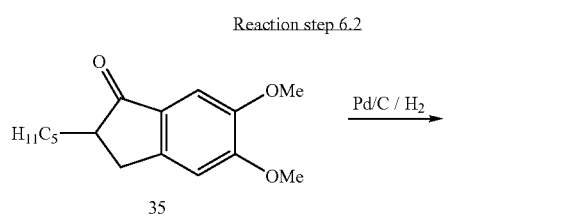

15.4 g (59 mmol) of the indanone 35 are dissolved in 150 ml of THF and hydrogenated at RT on a palladium catalyst. The hydrogenation solution is evaporated, and the residue is distilled under reduced pressure.

Reaction step 6.3

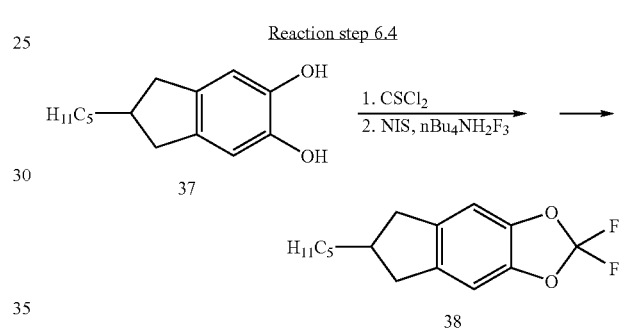

10 g (40 mmol) of the indane 36 are dissolved in 260 ml of dichloromethane under nitrogen, and 4.5 ml (47 mmol) of boron tribromide are added at RT. After 16 h at RT, the batch is added to 600 ml of 1M sodium hydroxide solution. The reaction mixture is subsequently acidified using hydrochloric acid. The organic phase is separated off and evaporated. The residue is the desired indane derivative 37.

Reaction step 6.4

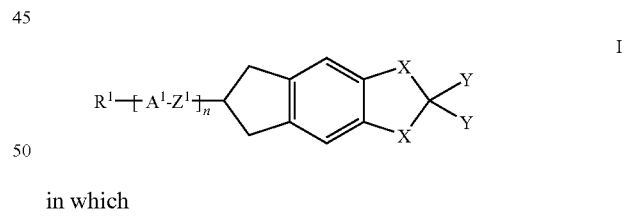

The synthesis of 38 from 37 is carried out as described by M. Kuroboshi, T. Hiyama *Synlett* (1994), 251-252.

The invention claimed is:

1. A 1,2,3,6,7,8-Hexahydro-s-indacene or 6,7-dihydro-5H-indeno[5,6-d]-1,3-dioxole compound of formula I

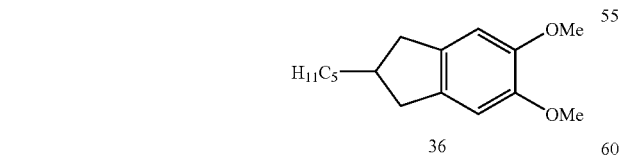

in which
R$^1$ denotes H, halogen, a linear or branched alkyl radical having 1 to 15 C atoms which is unsubstituted, monosubstituted by CN or CF$_3$ or at least monosubstituted by halogen and in which one or more CH$_2$ groups may each, independently of one another, be replaced by —O—, —S—, —CO—, —(CO)O—, —CH=CH—, —CH=CF—, —CF=CF— or —C≡C— in such a way that heteroatoms are not linked directly to one another and asymmetrical groups may be present in both orientations,
A$^1$ in each case, independently of one another, identically or differently, denotes
a) trans-1,4-cyclohexylene, in which one or more non-adjacent CH$_2$ groups may be replaced by —S—, tetrahydropyran-2,5-diyl or 1,3-dioxane-2,5-diyl, b) 1,4-phenylene, in which one or two CH groups may be replaced by N and in which one or more H atoms may be replaced by halogen,
c) a radical selected from the group consisting of 1,4-bicyclo[2.2.2]octylene, spiro[3.3]heptane-2,6-diyl, cyclobutane-1,3-diyl, piperidine-1,4-diyl, naphthalene-2,6-diyl, decahydronaphthalene-2,6-diyl and 1,2,3,4-tetrahydronaphthalene-2,6-diyl, in which CH may be replaced by N and in which one or more H atoms may be replaced by halogen, or
d) 1,4-cyclohexenylene, X denotes —CH$_2$—, —CF$_2$— or —O—,
Y denotes F, Cl, CF$_3$, CN, NCS, SCN, SF$_5$ or 2- to 6-C perfluoroalkyl,
Z$^1$ in each case, independently of one another, in the case of asymmetrical bridging units Z$^1$ in either of the two orientations, denotes a single bond, —CH$_2$O—, —(CO)O—, —CF$_2$O—, —CF=CF—, —CH$_2$CH$_2$CF$_2$O—, —CF$_2$CF$_2$—, —CH$_2$CF$_2$—, —CH$_2$CH$_2$—, —CH=CH—, —CH=CF— or —C≡C—, and
n denotes 0, 1, 2 or 3.

2. A compound according to claim 1, wherein Y denotes F or CF$_3$.

3. A compound according to claim 1 or 2, wherein n is equal to 0.

4. A compound according to claim 1 or 2, wherein n is equal to 1 and the compound of formula I is a compound of one of the following formulae

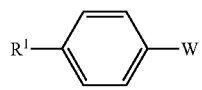 Iaa1

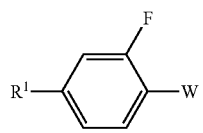 Iaa2

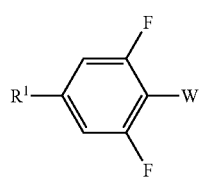 Iaa3

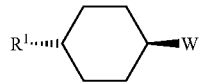 Iab1

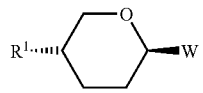 Iac1

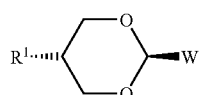 Iad1

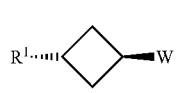 Iae1

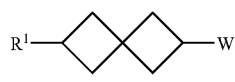 Iaf1 where W stands for the moiety of the following formula

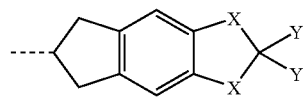 W in which
X denotes —CH$_2$—, —CF$_2$— or —O—, and
Y denotes F, Cl, CF$_3$, CN, NCS, SCN, SF$_5$ or 2- to 6-C perfluoroalkyl.

5. A compound according to claim 1 or 2, which has two rings in the mesogenic group R$^1$-[A$^1$-Z$^1$]$_n$—, selected from the group consisting of the compounds of formulae Ic, Id, Ie, and If

 Ic

 Id

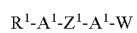 Ie

 If where W stands for the moiety of the following formula

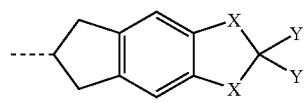 W in which
X denotes —CH$_2$—, —CF$_2$— or —O—, and
Y denotes F, Cl, CF$_3$, CN, NCS, SCN, SF$_5$ or 2- to 6-C perfluoroalkyl.

6. A compound according to claim 5, wherein the compound of formula Ic is one of the following formulae

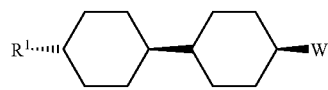 Ica1

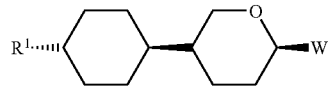 Icb1

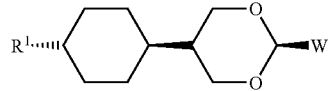 Icc1

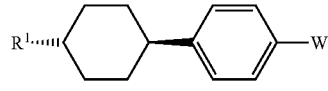 Icd1

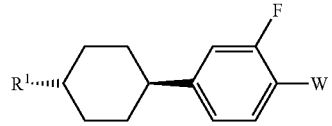 Icd2

-continued
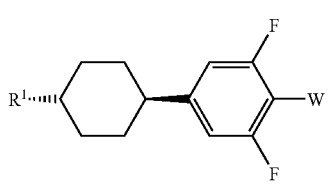
Icd3
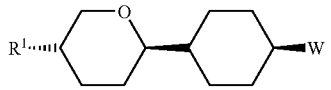
Ice1
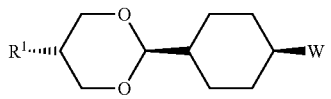
Icf1
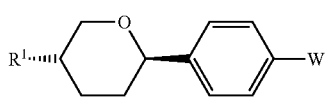
Ich1
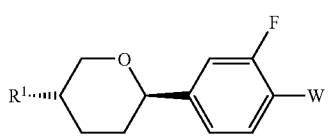
Ich2
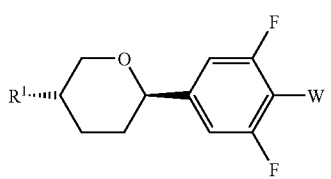
Ich3
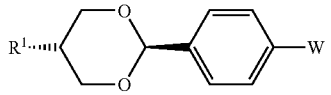
Ici1
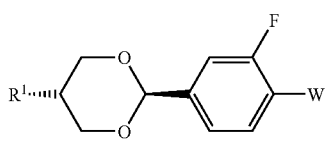
Ici2
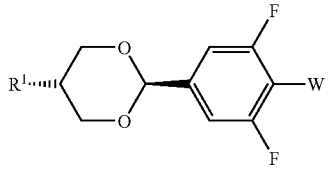
Ici3
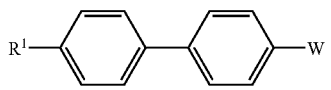
Icj1
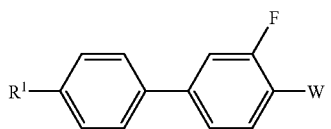
Icj2
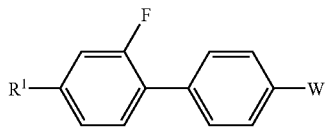
Icj3
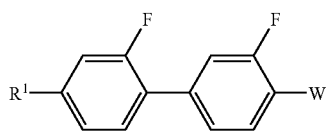
Icj4
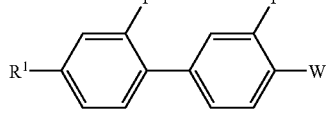
Icj5
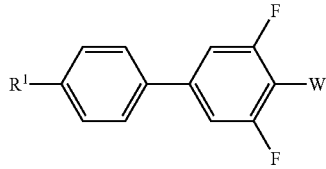
Icj6
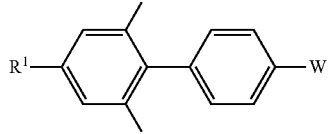
Icj7
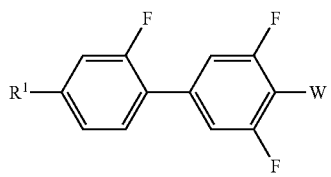
Icj8
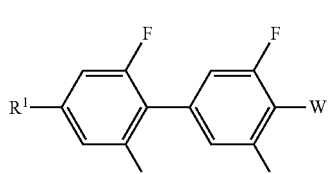
Icj9
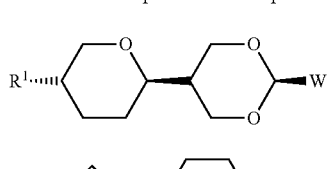
Icm1
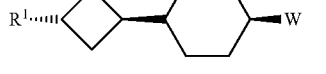
Icn1
Ico1
7. A compound according to claim 5, wherein the compound of formula Ie is one of the following formulae
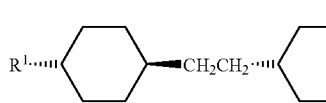
Iea1

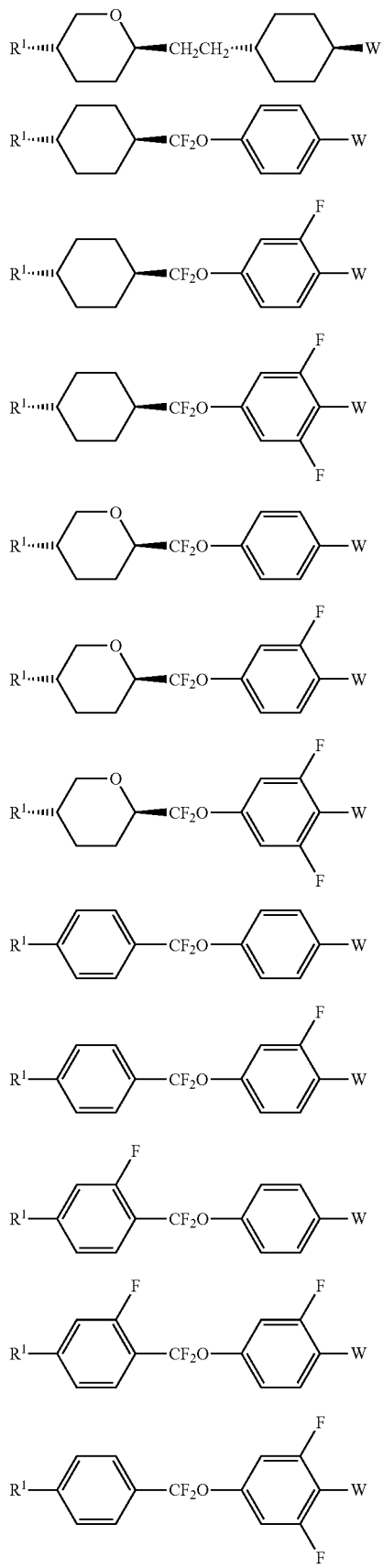
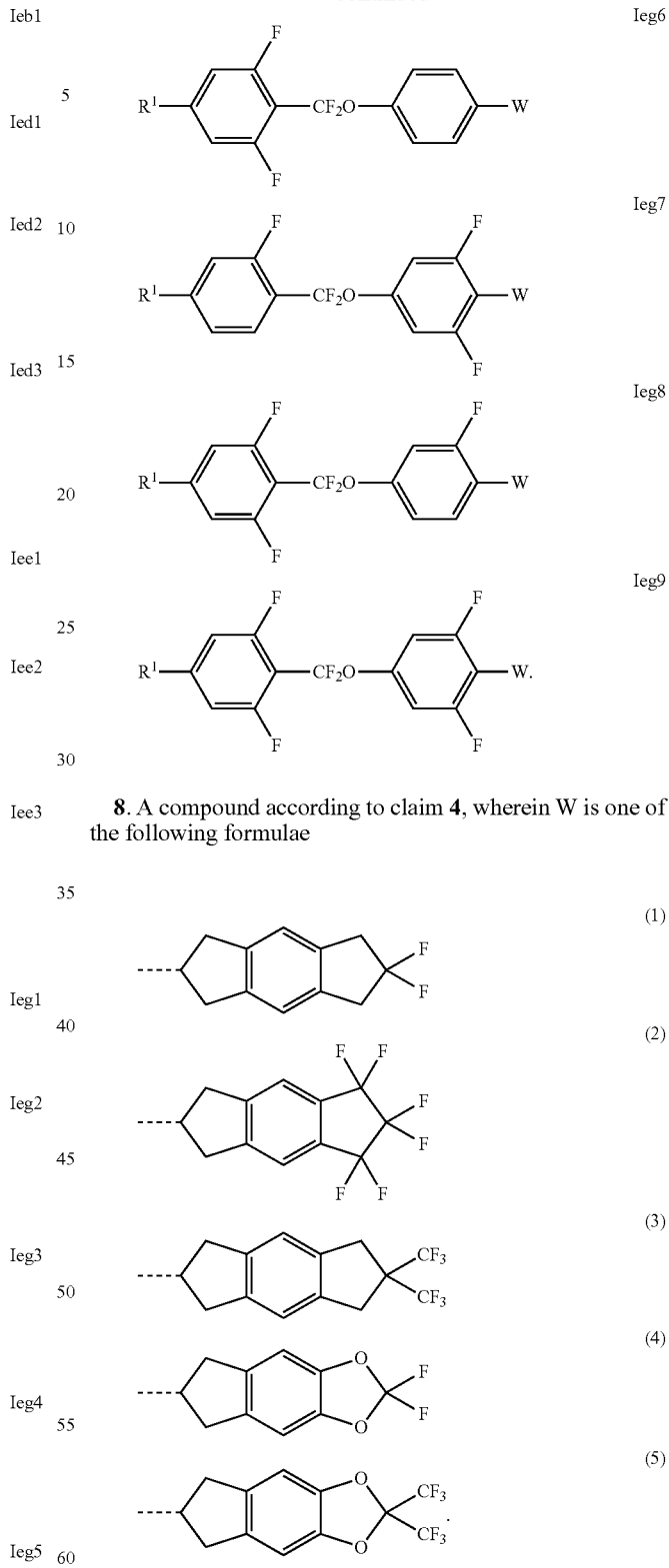
8. A compound according to claim 4, wherein W is one of the following formulae
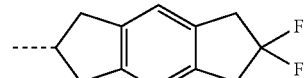
(1)
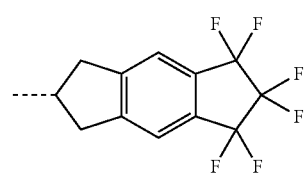
(2)
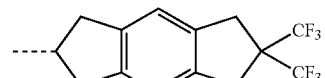
(3)
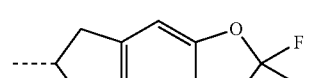
(4)
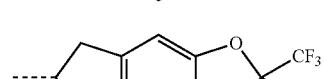
(5)
9. A compound according to claim 1, wherein $R^1$ denotes H, a linear alkyl or alkoxy radical having 1 to 12 C atoms or a linear alkenyl or alkenyloxy radical having 2 to 12 C atoms.
10. A liquid-crystalline media, comprising at least two liquid-crystalline components, one of which is a compound of claim 2.

11. A liquid-crystalline medium, comprising at least two liquid-crystalline components, one of which is at least one 1,2,3,6,7,8-hexahydro-s-indacene or 6,7-dihydro-5H-indeno[5,6-d]-1,3-dioxole compound according to claim 1.

12. A liquid-crystal display element, which contains a liquid-crystalline medium according to claim 11.

13. An electro-optical display element, which contains, as dielectric, a liquid-crystalline medium according to claim 11.

14. A process for preparing a compound of claim 1, comprising connecting a cyclopentane ring in the 5,6-position to a 5,6-dibromo or 5,6-dihydroxy compound of indane or of benzo-1,3-dioxole.

* * * * *